United States Patent
Brunicardi et al.

(10) Patent No.: US 9,644,205 B2
(45) Date of Patent: May 9, 2017

(54) SYNTHETIC PROMOTER FOR MODULATING GENE EXPRESSION

(71) Applicants: The Regents of the University of California, Los Angeles, CA (US); BAYLOR COLLEGE OF MEDICINE, Houston, TX (US)

(72) Inventors: Francis C. Brunicardi, Pacific Palisades, CA (US); Shi-He Liu, Sugarland, TX (US)

(73) Assignees: The Regents of the University of California, Oakland, CA (US); Baylor College of Medicine, Houston, TX (US)

(*) Notice: Subject to any disclaimer, the term of this patent is extended or adjusted under 35 U.S.C. 154(b) by 0 days.

(21) Appl. No.: 14/396,967

(22) PCT Filed: Apr. 24, 2013

(86) PCT No.: PCT/US2013/038068
§ 371 (c)(1),
(2) Date: Oct. 24, 2014

(87) PCT Pub. No.: WO2013/163346
PCT Pub. Date: Oct. 31, 2013

(65) Prior Publication Data
US 2015/0218555 A1    Aug. 6, 2015

Related U.S. Application Data

(60) Provisional application No. 61/637,971, filed on Apr. 25, 2012, provisional application No. 61/748,713, filed on Jan. 3, 2013.

(51) Int. Cl.
| | | |
|---|---|---|
| *C07H 21/04* | (2006.01) | |
| *C12N 15/63* | (2006.01) | |
| *C12N 15/113* | (2010.01) | |
| *C12N 15/11* | (2006.01) | |
| *C12N 15/85* | (2006.01) | |
| *C12N 15/70* | (2006.01) | |
| *C12N 15/81* | (2006.01) | |

(52) U.S. Cl.
CPC .......... *C12N 15/113* (2013.01); *C12N 15/111* (2013.01); *C12N 15/70* (2013.01); *C12N 15/81* (2013.01); *C12N 15/85* (2013.01); *C12N 2330/51* (2013.01); *C12N 2830/008* (2013.01); *C12N 2840/105* (2013.01)

(58) Field of Classification Search
None
See application file for complete search history.

(56) References Cited

U.S. PATENT DOCUMENTS

| | | | |
|---|---|---|---|
| 6,162,796 A | 12/2000 | Kaplitt et al. | |
| 6,642,053 B1 | 11/2003 | Daniell et al. | |
| 6,977,244 B2 | 12/2005 | Tormo et al. | |
| 7,063,947 B2 | 6/2006 | Hahm | |
| 7,125,902 B2 | 10/2006 | Shaw et al. | |
| 7,453,022 B2 | 11/2008 | Mahn et al. | |
| 7,592,320 B2 | 9/2009 | DeBenedetti et al. | |
| 2003/0213006 A1 | 11/2003 | Back et al. | |
| 2003/0219410 A1 | 11/2003 | Calatrava | |

FOREIGN PATENT DOCUMENTS

| | | |
|---|---|---|
| GB | 2355460 | 4/2001 |
| WO | 96-27676 | 9/1996 |
| WO | 01-23541 | 4/2001 |
| WO | 2011-109837 | 9/2011 |

OTHER PUBLICATIONS

Jenks, (Trends in Comparative Endocrinology and Neurobiology, 2009. Ann. N. Y. Acad. Sci. vol. 1163, pp. 17-30).*
Dickmeis, (Briefings in Functional Genomics and Proteomics, 2005. vol. 3, No. 4, pp. 332-350, see p. 341, 2nd col., lines 1-3).*
Wang et al. (Nucleic Acids Research, 2009. vol. 37, No. 8, pp. 2618-2629).*
Poole et al. (Gene, 2001. vol. 269, pp. 1-12).*
PCT International Search Report and Written Opinion dated Sep. 26, 2013 for PCT Application No. PCT/US2013/03868.
DeFatta, Robert et al. "Selective killing of cancer cells based on translational control of a suicide gene." Cancer Gene Therapy, 9, 573-578, 2002.
Grinnell, Brian W. et al. "Activation of the Adenovirus and BK Virus Late Promoters: Effects of the BK Virus Enhancer and trans-Acting Viral Early Proteins", Molecular and Cellular Biology, 3596-3605, Nov. 1986.
Liu, S et al. "Enhanced cytotoxicity of RIPTK gene therapy of pancreatic cancer via PDX-1 co delivery." Journal of Surgical Research. Jan. 2007.
Raty, J. et al. "Non-invasive Imaging in Gene Therapy", The American Society of Gene Therapy, vol. 15, No. 9, 1579-1586, 2007.
Taniguchi, H. et al. "β-cell neogenesis induced by adenovirus-mediated gene delivery of transcription factor pdx-1 into mouse pancreas", Gene Therapy,10,15-23, 2003.
Vile, R. et al. "Use of Tissue-specific Expression of the Herpes Simplex Virus Thymidine Kinase Gene to Inhibit Growth of Established Murine Melanomas following Direct Intratumoral Injection of DNA", Cancer Research, 53, 3860-3864, Sep. 1993.
Yang, Li et al. "Gene Therapy of Metastatic Pancreas Cancer with Intraperitoneal Injections of Concentrated Retroviral Herpes Simplex Thymidine Kinase Vector Supernatant and Ganciclovir", Annals of Surgery, vol. 224, No. 3, 405-417, 1996.

* cited by examiner

*Primary Examiner* — Celine Qian
(74) *Attorney, Agent, or Firm* — Gates & Cooper LLP

(57) ABSTRACT

The present invention provides nucleic acid constructs, expression vectors, transgenic cell and methods of making and using the same, wherein the nucleic acid construct includes a synthetic promoter designed using selected PDX-1 activation sites such as those observed in the human insulin promoter (HIP). In illustrative working embodiments of the invention, an exogenous nucleic acid fragment encoding thymidine kinase is operably linked to the synthetic promoter which is then shown to regulate the expression of this polypeptide.

10 Claims, 12 Drawing Sheets

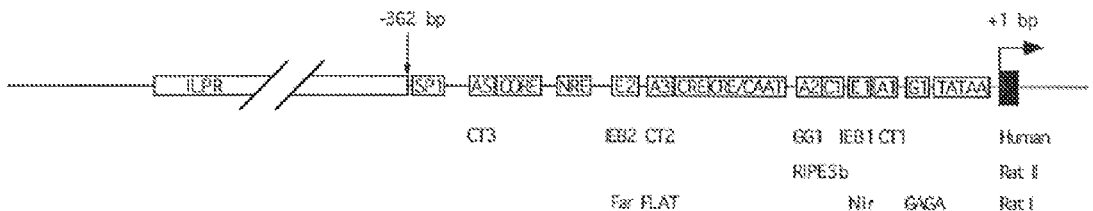

FIGURE 1A

GACAGCAGCGCAAAGAGCCCCGCCCTGCAGCCTCCAGCTCTCCTGGTC
TAATGTGGAAAGTGGCCCAGGTGAGGGCTTTGCTCTCCTGGAGACATTT
GCCCCCAGCTGTGAGCAGGGACAGGTCTGGCCACCGGGCCCCTGGTTA
AGACTCTAATGACCCGCTGGTCCCAGGGACAGGTCTGGCCACCGGGCC
CCTGGTTAAGACTCTAATGACCCGCTGGTCCCAGGGACAGGTCTGGCC
ACCGGGCCCCTGGTTAAGACTCTAATGACCCGCTGGTCCGGAAATGGT
CCGGAAATTGCAGCCTCAGCCCCCAGCCATCTGCCGACCCCCCACCCC
AGGCCCTAATGGGCGGAAATGGTCCGGAAATTGCAGCCTCAGCCCCCA
GCCATCTGCCGACCCCCCACCCCAGGCCCTAATGGGCGGAAATGGTC
CGGAAATTGCAGCCTCAGCCCCCAGCCATCTGCCGACCCCCCACCCCA
GGCCCTAATGGGCGGTAGGGGAGATGGGCTCTGAGACTATAAAGCCAG
CGGGGGCCCAGCAGCCCTC  (SEQ ID NO: 1)

FIGURE 1B

```
ACAGGGGTGTGGGGACAGGGGTGTGGGGACAGGGGTCTGGGGACAGGGGTGTGGGGACAGGGGTCCTGGG
GACAGGGGTGTGGGGATAGGGGTGTGGGGACAGGGGTGTGGGGACAGGGGTGTGGGGACAGGGGTCTGGG
GACAGCAGCGCAAAGAGCCCCGCCCTGCAGCCTCCAGCTCTCCTGGTCTAATGTGGAAAGTGGCCCAGGT
                                                    A5      Enhancer core
GAGGGCTTTGCTCTCCTGAGACATTTGCCCCAGCTGTGAGCAGGGACAGGTCTGGCCACC     CT
           Negative regulatroy element          C2        E2        G2
GGTTAAGACTCTAATGACCCGCTGGTCCTGAGGAAGAGGTGCTGACGACCAAGCAGATCTTCCCACAGAC
        A3       CRE1                          CRE2
CCAGCACCAGGGAAATGGTCCCGAAATTGCAGCCTCAGCCCCAGCCATCTGCGGACCCCCCCACCCCAG
     GG2       GG1/A2      C1                E1
GCCCTAATGGGCCAGGCGGCAGGGGTTGAGAG  AGGGGAGATGGGCTCTGAGACTATAAAGCCAGCGGG
   A1                         G1                        TATA box
GGCCCAGCAGCCCTC    TCCAGGACAGGCGCATCAGAAGAGGCCATCAAGCAGGTCTGTTCCAAGG
    +1 Start of transcription        CRE3
GCCTTTCCGTCAGGTGGCCAGGATTCCAGGGTGGCTGGACCCCAGGCCCCAGCTCTGCAGCAGGGAGG
      CRE4
ACGTGGCTGGGCTCGTGAAGCATGTGGGGGTGAGCCCAGGGGCCCCAAGGCAGGGCACCTGGCCTTCAGC
```

(SEQ ID NO: 2)

FIGURE 1C

GACAGCAGCGCAAAGAGCCCCGCCCTGCAGCCTCCAGCTCTCCTGGTC
TAATGTGGAAAGTGGCCCAGGTGAGGGCTTTGCTCTCCTGGAGACATTT
GCCCCAGCTGTGAGCAGGGACAGGTCTGGCCACCGGGCCCCTGGTTA
AGACTCTAATGACCCGCTGGTCCCAGGGACAGGTCTGGCCACCGGGCC
CCTGGTTAAGACTCTAATGACCCGCTGGTCCCAGGGACAGGTCTGGCC
ACCGGGCCCCTGGTTAAGACTCTAATGACCCGCTGGTCCCAGGGACAG
GTCTGGCCACCGGGCCCCTGGTTAAGACTCTAATGACCCGCTGGTCCCA
GGGACAGGTCTGGCCACCGGGCCCCTGGTTAAGACTCTAATGACCCGC
TGGTCCCTATAAAGCCAGCGGGGGCCCAGCAGCCCTC (SEQ ID NO: 3)

SYNTHETIC PROMOTER FOR MODULATING GENE EXPRESSION

CROSS-REFERENCE TO RELATED APPLICATIONS

This application claims the benefit under 35 U.S.C. Section 119(e) of U.S. Provisional Patent Application Ser. No. 61/637,971 filed Apr. 25, 2012, and U.S. Provisional Patent Application Ser. No. 61/748,713 filed Jan. 3, 2013 both entitled "SYNTHETIC PROMOTER FOR MODULATING GENE EXPRESSION" the contents of each which are incorporated herein by reference.

STATEMENT OF FEDERALLY FUNDED RESEARCH

This invention was made with Government support under CA095731, awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 25, 2015, is named 30435.254-US-WO_SL.txt and is 6,933 bytes in size.

TECHNICAL FIELD OF THE INVENTION

The present invention relates generally to compositions and methods for modulating gene expression and/or the activity of a novel, synthetic gene promoter.

BACKGROUND OF THE INVENTION

Expression vectors have been used for decades as vehicles for the expression of genes or cDNAs encoding polypeptides or proteins of interest in host cells. With such vectors, viral or cellular promoters are typically used to express a gene of interest in selected host cells. For example, by using tissue specific promoters, one can selectively turn on genes in specific cell lineages, a important goal in gene therapy. For example, strategies can use a cell specific promoter to activate a suicide gene only in the targeted tumor cells.

U.S. Pat. No. 7,592,320 discloses a cancer gene therapy based on translational control of a suicide gene that does not require specific knowledge of the cancer cells, but instead targets a general characteristic that distinguishes cancer cells from normal cells, i.e., elevated eIF4E expression. The expression of a toxin or conditional toxin such as HTK is translationally repressed in normal cells by placing a complex 5' UTR in front of its reading frame. In prototype experiments, this HTK mRNA, a transcriptional product of the BK-viralTK vector, was translationally regulated so as to largely inhibit its production in normal murine and human cells, while cancer cells efficiently translated the protein, resulting in increased sensitivity to ganciclovir (GCV). Synthesis of the HTK protein from the BK-viralTK vector containing the 5' UTR of Fibroblast growth factor-2 ("FGF-2") readily occurred in a panel of murine and human breast carcinoma lines, but not in normal cell lines. Subcutaneous tumors and experimental lung metastases of the breast carcinoma line MM2MT in BALB/c mice were greatly reduced by transfection with the BK-viralTK vector, followed by GCV administration. Both the BK-viralTK and the BK-TK (control) vectors were effective in reducing lung metastasis following systemic delivery of the vectors and subsequent GCV administration. However, the BK-TK vector was highly toxic to mice while little to no toxicity was seen in mice treated with the BK-viralTK vector.

U.S. Pat. No. 7,453,022 discloses a method of increasing the content of selected transgene-coded proteins or peptides in plants and includes a method of increasing the content of one or more transgene-coded proteins or peptides in a plant. The increase is an effect of a decrease in the concentration of an ATP/ADP transporter in the plant. The method depends on transformation with and expression of a cDNA encoding an ATP/ADP transporter operably linked in antisense orientation to a promoter active in the plant.

U.S. Pat. No. 7,125,902 discloses methods, compounds, and diagnostics for cancer treatment and includes methods of treating cancer employing isoxazole derivatives. Compounds and methods of using these compounds for isolating and/or detecting binding proteins, which may be indicative of a disease, are also described.

U.S. Pat. No. 6,977,244 discloses the inhibition of Bcl-2 protein expression by liposomal antisense oligodeoxynucleotides and provides compositions and methods for use in the treatment of Bcl-2-associated diseases like cancer, specifically, in the treatment of follicular lymphoma (FL). The compositions contain antisense oligonucleotides that hybridize to Bcl-2 nucleic acids, the gene products of which are known to interact with the tumorigenic protein Bcl-2. Used alone, or in conjunction with other antisense oligonucleotides, these compositions inhibit the proliferation of FL cancer cells.

SUMMARY OF THE INVENTION

The present invention relates to synthetic promoters and methods for making and using them. Embodiments of the invention include, for example, a nucleic acid construct comprising a synthetic promoter and a nucleic acid operably linked to this promoter that regulates the expression of this exogenous nucleic acid. As discussed in detail below, embodiments of the invention use expression vectors having the synthetic promoters disclosed herein to modulate the expression of a wide variety of genes in various cells including human cancer cells.

Embodiments of the invention include methods for regulating expression of an exogenous protein in one or more cells by providing an expression vector comprising a BL promoter and an exogenous nucleic acid fragment operably linked to the BL promoter, wherein the BL promoter regulates the expression of an exogenous nucleic acid fragment; transforming one or more cells with the expression vector; and expressing the exogenous nucleic acid fragment. The present invention also provides a method for selectively expressing a toxin within a cell by administering an expression vector comprising a BL promoter and an exogenous nucleic acid fragment operably linked to the BL promoter, wherein the BL promoter regulates the expression of an exogenous nucleic acid fragment; transforming one or more cells with the expression vector; and expressing the exogenous nucleic acid fragment.

Other embodiments of the invention include nucleic acid constructs having selected transcriptional motifs such as a BL promoter comprising at least one E2 motif SEQ ID NO: 7 GCCACCGG operably connected to at least one A1 motif SEQ ID NO: 13 TAAT. In one aspect, the construct further comprises at least one BL promoter motif in communication with at least one E2 motif SEQ ID NO: 7 GCCACCGG and to at least one A1 motif SEQ ID NO: 13 TAAT, wherein the at least one BL promoter motif is selected from an Enhancer core SEQ ID NO: 5 TGGAAAG; a C2 motif SEQ ID NO: 6 CAGGGACAGG; a E2 motif SEQ ID NO: 7 GCCAC-CGG; a G2 motif SEQ ID NO: 8 GGGCCC; a GG2 motif SEQ ID NO: 9 GGAAAT; a GG1/A2 motif SEQ ID NO: 10 GGAAAT; a C1 motif SEQ ID NO: 11 TGCAGCCTCA-GCC; a E1 motif SEQ ID NO: 12 GCCATCTGCC; a A1 and A3 motif SEQ ID NO: 13 TAAT; a G1 motif SEQ ID NO: 15 GTAGGGGA; a CRE 1 motif SEQ ID NO: 16 GAC-CCGCTGGTCC; a CRE 2 motif SEQ ID NO: 17 TGAC-GACCAAGGAGATC; a CRE 3 motif SEQ ID NO: 18 TGCATCAGAAGAG; and a CRE 4 motif SEQ ID NO: 19 TGCGTCAGGTGGGCT.

Yet another embodiment of the invention includes a method for regulating expression of an exogenous protein in one or more cells comprising the steps of: providing an expression vector comprising a BL promoter and an exogenous nucleic acid fragment operably linked to the BL promoter, wherein the BL promoter regulates the expression of an exogenous nucleic acid fragment; transforming one or more cells with the expression vector; and expressing the exogenous nucleic acid fragment. In one aspect, the heterologous protein is transiently over-expressed. In another aspect, the BL promoter is a BL-1 promoter, a BL-4 promoter or both.

Yet another embodiment of the present invention includes a method for selectively expressing a toxin within a cell comprising the steps of combining the cell with an expression vector comprising a BL promoter and an exogenous nucleic acid fragment operably linked to the BL promoter. In such embodiments of the invention, the cell is selected to be one where the BL promoter regulates the expression of an exogenous nucleic acid fragment to which it is operably linked. Such methods can include transforming one or more cells with the expression vector; and expressing the exogenous nucleic acid fragment with the BL promoter. In one aspect, the step of administering an expression vector is defined further as providing a cell with an amount of the exogenous nucleic acid fragment effective to inhibit cellular metabolism or growth.

The present invention also provides a method of treatment for a cancer by providing a patient in need of cancer treatment; administering a therapeutically effective amount of an expression vector to the patient, wherein the expression vector comprises a BL promoter and an exogenous nucleic acid fragment operably linked to the BL promoter, wherein the BL promoter regulates the expression of an exogenous nucleic acid fragment; transforming one or more cells of the patient with the expression vector; and expressing the exogenous nucleic acid fragment in the one or more cells of the patient, wherein the exogenous nucleic acid fragment is transcribed under conditions that exist within tumor cells to produce a messenger RNA sequence that comprises a translatable sequence encoding a protein.

Yet another embodiment of the present invention includes a method of treatment for a cancer comprising the steps of: providing a patient in need of cancer treatment; administering an therapeutically effective amount of an expression vector to the patient, wherein the expression vector comprises a BL promoter and an exogenous nucleic acid fragment operably linked to the BL promoter, wherein the BL promoter regulates the expression of an exogenous nucleic acid fragment into a protein; transforming one or more cells of the patient with the expression vector; and expressing the exogenous nucleic acid fragment in the one or more cells of the patient, wherein the exogenous nucleic acid fragment is transcribed under conditions that exist within tumor cells to produces a messenger RNA sequence that comprises a translatable sequence encoding a protein. In one aspect, the protein comprises a herpes thymidine kinase toxin. In another aspect, the cancer is a metastatic tumor, a solid tumor or both. In another aspect, the cancer is a metastatic tumor selected from the group consisting of bladder, breast, cervical, colon, lung, prostate, and head and neck.

The working embodiments of the invention that are disclosed herein demonstrate that a pancreas homing platform using the BL promoter was as effective as the cytomegalovirus (CMV) promoter in driving gene expression in cells expressing PDX-1, cells which include most solid cancers, cells in the islets of Langerhans, as well as acinar, ductal, and progenitor/stem cells of the pancreas. Any gene/RNAi therapy can be delivered specifically to these PDX-1 expressing cells using the platform comprising, e.g., a pUMVC3 backbone, microRNA 30 backbone delivered by decorated, reversibly masked liposomes. The platform can be used for ex vivo treatment of cancer cells and islets, as well as multiple cycles of intravenous therapy in patients.

The BL promoter of the present invention may be used to drive expression of MafA-2A-NgN3 in pancreatic tissues to generate islets from acinar tissues. Since BL will drive expression in PDX-1 expressing cells, it was suggested that the doublet BL-MafA-2A-Ngn3 plasmid would be required to transform acinar cells into islets, as opposed to delivering a BL-PDX-1-2A-MafA-NgN3 triplet plasmid. The BL promoter may replace CMV in the pUMVC3 vector backbone being used to drive expression of selected genes or bi-shRNA for clinical trials.

Furthermore, the BL promoter can be used to improve selectivity of existing plasmids to target PDX-1 expressing tissues, which would include most cancers and islets. Other examples include, e.g., BL-bi-shRNA Statmin-1 and BL-bi-shRNA PDX-1 and BL-bi-shRNAi Furin, in order to potentially improve selectivity of these plasmids to target cancers and islets using intravenous delivery.

Based upon of in vitro and in vivo studies using the rat insulin promoter to drive expression in mouse models of pancreas cancer, insulinoma and islet hyperplasia, the development of novel plasmids, such as BL-vTK and/or BL-SSTR5 for theranostics (combined term for imaging and therapy) of cancer and diabetes is made possible using the present invention. Both vTK and SSTR5, along with their respective prodrugs/peptides, can be used for both PET/CT/MRI/Optical imaging and for therapy.

BRIEF DESCRIPTION OF THE DRAWINGS

For a more complete understanding of the features and advantages of the present invention, reference is now made to the detailed description of the invention along with the accompanying figures and in which:

FIG. 1A is an image of the promoter sequence elements in the insulin promoter;

FIG. 1B a sequence of the BL1 promoter sequence SEQ ID NO: 1;

FIG. 1C a sequence of the BL1 promoter sequence showing the promoter elements SEQ ID NO: 2;

FIG. 1D a sequence of the BL4 promoter sequence SEQ ID NO: 3;

DETAILED DESCRIPTION OF THE INVENTION

Figure 2:
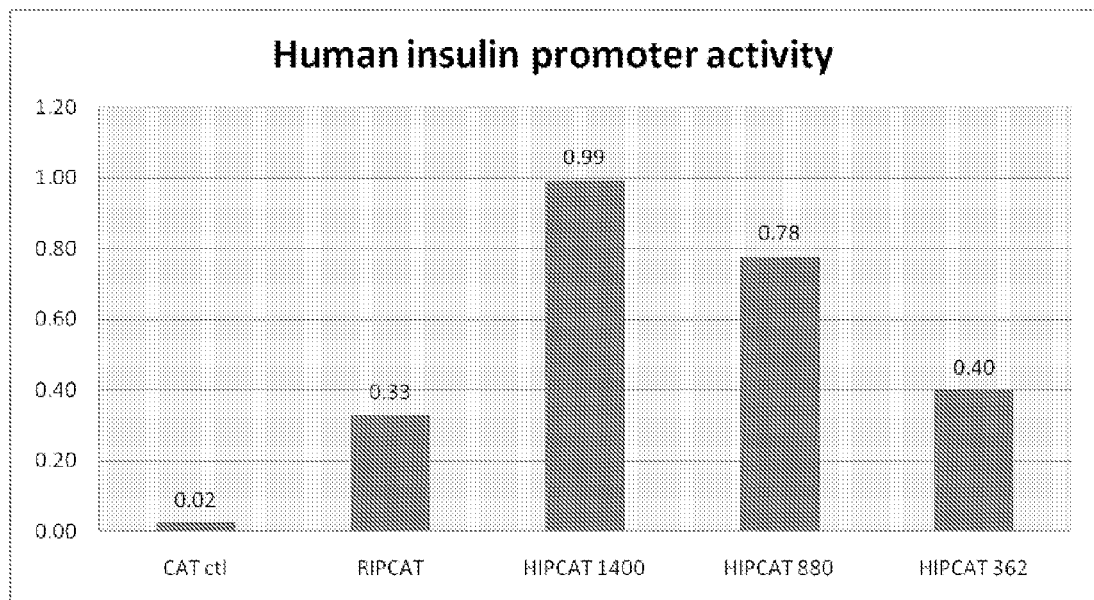
FIG. 2 is a plot of the CAT assay for HIP activity in Beta TC-6 cells.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a synthetic DNA promoter sequence which can be operably linked to a nucleic acid sequence so that this nucleic acid sequence is transcribed in a cell. In specific embodiments, the DNA promoter sequence of the present invention is generally positioned upstream of the nucleic acid sequence transcribed to produce DNA, RNA, mRNA, siRNA or shRNA, and provides a site for specific binding by RNA polymerase and other transcription factors. For example, regulatory elements of the BL promoter can include C2, E2, G2, A3, CRE1, CRE2, GG2, GG1, A2, C1, E1, A1, G1 domains and various repeats and arrangements thereof. Embodiment of the DNA promoter sequence of the present invention can include various repeats and arrangements thereof, for example, C2/E2/G2/A3/CRE1 and GG2/A2/C1/E1/A1 or one, two or three repeated of C2/E2/G2/A3/CRE1 and one, two or three repeated of GG2/A2/C1/E1/A1.

The invention disclosed herein has a number of embodiments. Illustrative embodiments of the invention include a nucleic acid comprising a BL promoter having at least one copy of a nucleotide sequence comprising an E2 motif and an A3 motif ("E2/A3"), for example one where E2 comprises GCCACCGG (SEQ ID NO: 7) and A3 comprises TAAT (SEQ ID NO: 13). In such embodiments of the invention, the BL promoter modulates transcription of an exogenous nucleic acid operatively linked to this promoter. Another embodiment of the invention is a nucleic acid comprising a BL promoter having at least one, two or three copies of a nucleotide sequence comprising GG2/A2/C1/E1/A1, wherein GG2 comprises GGAAAT (SEQ ID NO: 9), A2 comprises GGAAAT (SEQ ID NO: 10), C1 comprises TGCAGCCTCAGCC (SEQ ID NO: 11), E1 comprises GCCATCTGCC (SEQ ID NO: 12), and A1 comprises TAAT (SEQ ID NO: 13). Embodiments of the invention include compositions of matter comprising the nucleic acids disclosed herein in combination with a pharmaceutically acceptable carrier. In certain embodiments of the invention, this BL promoter embodiment modulates transcription of an exogenous nucleic acid operatively linked to the BL promoter by increasing transcription by at least 10%, 25%, or 50% as compared to a comparable promoter having only one or two copies of a nucleotide sequence comprising GG2/A2/C1/E1/A1. In certain embodiments of the invention, the promoter has a minimal size and is at least 100, 200, 300, or 400 nucleotides. In other embodiments of the invention, the promoter has a maximal size and is less than 200, 300, 400 or 500 nucleotides.

In certain embodiments of the invention, the BL promoter further includes E2/A3 and/or GG2/A2/C1/E1/A1, as well as at least one of the other motifs disclosed herein, for example C2, E2, G2, A3, CRE1, CRE2, CRE3, G1 or an enhancer core. In typical embodiments of the invention, a TATA Box comprises TATAAA (SEQ ID NO. 4), an Enhancer core comprises TGGAAAG (SEQ ID NO: 5), a C2 motif comprises CAGGGACAGG (SEQ ID NO: 6), a E2 motif comprises GCCACCGG (SEQ ID NO: 7), a G2 motif comprises GGGCCC (SEQ ID NO: 8), a GG2 motif comprises GGAAAT (SEQ ID NO: 9), a GG1/A2 motif comprises GGAAAT (SEQ ID NO: 10), a C1 motif comprises TGCAGCCTCAGCC (SEQ ID NO: 11), a E1 motif comprises GCCATCTGCC (SEQ ID NO: 12), an A1 motif comprises TAAT (SEQ ID NO: 13), an A3 motif comprises GGCG (SEQ ID NO: 14), a G1 motif comprises GTAGGGGA (SEQ ID NO: 15), a CRE 1 motif comprises GACCCGCTGGTCC (SEQ ID NO: 16), a CRE 2 motif comprises TGACGACCAAGGAGATC (SEQ ID NO: 17), a CRE 3 motif comprises TGCATCAGAAGAG (SEQ ID NO: 18), a CRE 4 motif comprises TGCGTCAGGTGGGCT (SEQ ID NO: 19), a C2 comprises CAGGGACAGG (SEQ ID NO: 6), a E2 comprises GCCACCGG (SEQ ID NO: 7). Embodiments of the BL promoter include one or more constellation of motifs disclosed herein such as 1, 2, 3, 4, 5 or more copies of a nucleotide sequence comprising E2/A3, or A2/E1/A1, or C2/E2/G2/A3/CRE1. Specific working embodiments of the invention having these motifs include a BL-1 promoter (SEQ ID NO: 1) as well as a BL-4 promoter (SEQ ID NO: 3).

Figure 14:
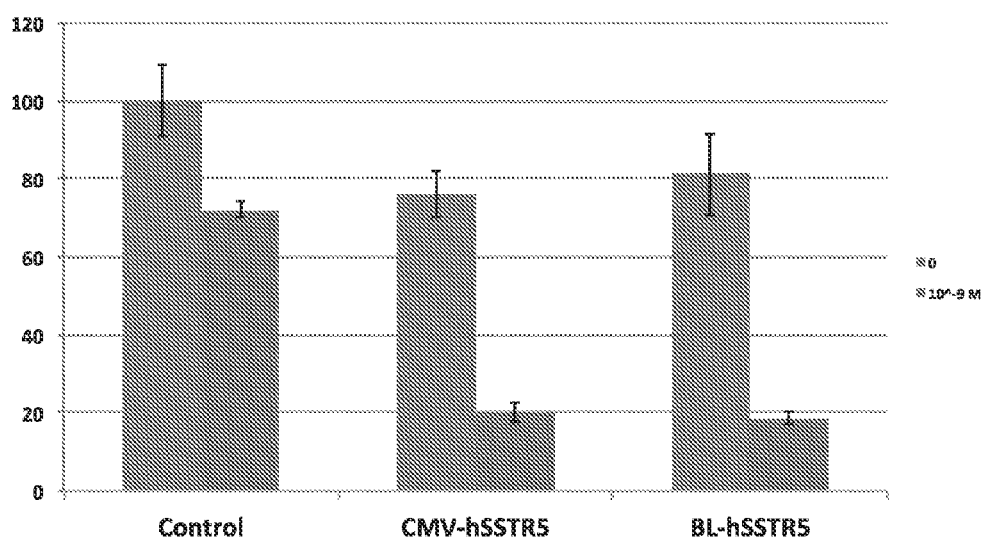
FIG. 14 is a plot illustrating comparing promoter activities and antiproliferative effect of BL-SSTR5 and somatostatin receptor 5 analog versus CMV-SSTR and somatostatin receptor 5 analogue in HEK-293-PDX-1 overexpressing cells.
Figure 15:
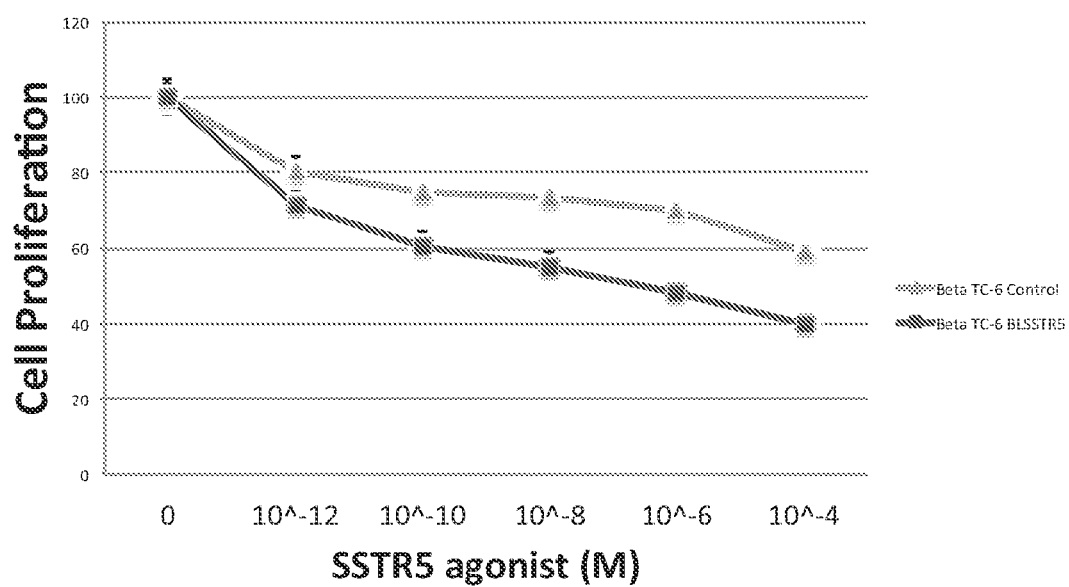
FIG. 15 is a plot comparing promoter activities and antiproliferative effect of BL-SSTR5 and differing doses of somatostatin receptor 5 analogue versus CMV-SSTR and differing doses of somatostatin receptor 5 analogue in Beta TC 6 cells.

In aspects of the invention, a heterologous nucleic acid (i.e. a nucleic acid that does not encode human insulin) is operatively linked to the BL promoter. Optionally, the heterologous nucleic acid encodes a polypeptide having an ability to modulate growth of a cell expressing said polypeptide. A variety of genes can be linked to the BL promoter. Illustrative proteins encoded by genes that can be driven by the BL promoter include any one of the five somatostatin receptors (SSTR 1-5). Illustrative data from an embodiment of the invention where the BL promoter is used to drive SSTR5 is shown in FIGS. 14 and 15. Other illustrative heterologous proteins include Furin, GM-CSF and Stathmin1.

Embodiments of the invention include sequences, vectors and methods that are designed to inhibit the expression of an endogenous gene, for example by using a BL promoter driven shRNA. In one illustration of this, one can inhibit the expression of the STAT3 protein by using BL-STAT3 shRNA. In addition, certain embodiments of the invention include combination vectors, in which multiple gene targets are either delivered and/or knocked down using embodiments of the BL promoter.

Embodiments of the invention include expression vectors comprising the promoters disclosed herein. Optionally, the expression vector includes a gene operably linked to control sequences recognized by one or more non-human host cells that can be transformed with the vector (e.g. a Shine-Dalgarno sequence). Related embodiments of the invention include a host cell comprising the expression vectors disclosed herein. Typically, the host cell is an *Escherichia coli*, yeast or human cell. Embodiments of the invention also include methods for expressing an exogenous nucleic acid in one or more cells using an expression vector comprising a BL promoter and an exogenous nucleic acid operably linked to the BL promoter. Typically in such embodiments, the BL promoter includes at least three copies of a nucleotide sequence comprising GG2/A2/C1/E1/A1, wherein GG2 comprises GGAAAT (SEQ ID NO: 9), A2 comprises GGAAAT (SEQ ID NO: 10), C1 comprises TGCAGCCTCAGCC (SEQ ID NO: 11), E1 comprises GCCATCTGCC (SEQ ID NO: 12), and A1 comprises TAAT (SEQ ID NO: 13). These methods comprise transforming one or more cells with a expression vector disclosed herein so that this cell expresses an exogenous nucleic acid fragment (e.g. by growing the cell under conditions selected so that the cell transcribes and translates a protein such as thymidine kinase). Optionally, the BL promoter further includes at least one nucleotide sequence comprising a C2, E2, G2, A3, CRE1, CRE2, CRE3, or G1 motif or an enhancer core. In certain embodiments of the invention, the expression vector includes at least one, two or three copies of a nucleotide sequence comprising E2/A3, A2/E1/A1 or C2/E2/G2/A3/CRE1. A related embodiment of the invention is a method of transforming a cell by combining the cell with an expression vector comprising a polynucleotide regulatory sequence operably linked to an exogenous nucleic acid sequence so that the cell is transformed with the vector and expresses the exogenous nucleic acid sequence. In illustrative embodiments of the invention, the cell is human PDX-1-expressing cell; a mammalian cancer cell, a mammalian stem cell or a cell present in the islets of Langerhans.

In certain embodiments of the invention, the polynucleotide regulatory sequence regulates the expression of the exogenous nucleic acid sequence; and expression of the exogenous nucleic acid sequence is selected to enhance a process for imaging the cell; and/or to alter a metabolic process in the cell. In an illustrative embodiment of the invention, the expression vector expresses a gene that facilities a positron emission tomography (PET) or magnetic resonance imaging (MRI) process. In another illustrative working embodiment of the invention, the expression vector encodes a suicide gene under the control of the BL promoter which alters the metabolism of the cell.

Embodiments of the invention include constellations of the motif sequences disclosed herein. Exemplary constellations of sequences include, for example, E2/A3, A2/E1/A1, C2/E2/G2/A3/CRE1 and GG2/A2/C1/E1/A1. In certain aspects, the constellations of sequences can be repeated 2, 3, 4, 5, 6, 7, 8, 9, 10 or more times. For example, BL promoter 1 comprises three repeated C2/E2/G2/A3/CRE1 constellations and three repeated GG2/A2/C1/E1/A1 constellations. The inventors have also determined that the A box and E box can be significant elements for the activation of insulin promoter in certain embodiments of the invention, and that a repeated A/E mini enhancer constellation can induce enhanced promoter activity. The A/E mini enhancer can be repeated 2, 3, 4, 5, 6, 7, 8, 9 or even 10 or more times.

In another illustrative embodiment of the invention, the BL 4 promoter includes five repeated C2/E2/G2/A3/CRE1 constellations. In this example, the core sequence is E2/A3 (E2 motif SEQ ID NO: 7 GCCACCGG+A3 motif SEQ ID NO: 13 TAAT), which may or may not include any spacer sequences, e.g., those shown in FIGS. 1B to 1D. The present invention includes a nucleic acid construct having promoter activity with a BL promoter at least one motif selected from a TATA Box SEQ ID NO: 4 TATAAA; Enhancer core SEQ ID NO: 5 TGGAAAG; C2 motif SEQ ID NO: 6 CAGGGACAGG; E2 motif SEQ ID NO: 7 GCCACCGG; G2 motif SEQ ID NO: 8 GGGCCC; GG2 motif SEQ ID NO: 9 GGAAAT; GG1/A2 motif SEQ ID NO: 10 GGAAAT; C1 motif SEQ ID NO: 11 TGCAGCCTCAGCC; E1 motif SEQ ID NO: 12 GCCATCTGCC; A1 and A3 motif SEQ ID NO: 13 TAAT; SEQ ID NO: 14 GGCG; G1 motif SEQ ID NO: 15 GTAGGGGA; CRE 1 motif SEQ ID NO: 16 GACCCGCTGGTCC; CRE 2 motif SEQ ID NO: 17 TGACGACCAAGGAGATC; CRE 3 motif SEQ ID NO: 18 TGCATCAGAAGAG; and CRE 4 motif SEQ ID NO: 19 TGCGTCAGGTGGGCT.

As used herein, the term "antibody" herein is used in its broadest sense and illustratively includes polyclonal antibodies, monoclonal antibodies, chimeric antibodies, humanized antibodies, as well as antigen binding antibody fragments and molecules having PDX-1 binding functionality. The term "antibody" includes an intact immunoglobulin having four polypeptide chains, two heavy (H) chains, and two light (L) chains linked by disulfide bonds. The term antibody also includes "antigen binding antibody fragments" illustratively including such fragments as an Fab fragment, an Fab' fragment, an F(ab')2 fragment, an Fd fragment, an Fv fragment, an scFv fragment, and a domain antibody (dAb). In addition to uses as anti-PDX-1 agents, an antibody is optionally included in inventive compositions and methods to target an anti-PDX-1 agent to a specified location as described further below. Antibodies are generated using standard techniques, using PDX-1 or peptides corresponding to portions of PDX-1 as an antigen. Methods of antibody generation are described in detail in E. Harlow and D. Lane, Antibodies: A Laboratory Manual, Cold Spring Harbor Laboratory Press, 1988; and B. K. C. Lo, Antibody Engineering: Methods and Protocols (Methods in Molecular Biology) Humana Press, December 2003.

As used herein, the term "tumor" in its broadest sense refers to neoplastic growth of cells of various types, illustratively including, but not restricted to squamous cell carcinoma; basal cell carcinoma; transitional cell carcinoma; adenocarcinoma; gastrinoma; cholangiocellular carcinoma; hepatocellular adenoma; hepatocellular carcinoma; renal cell carcinoma; melanoma; fibrosarcoma; myxosarcoma; liposarcoma; leiomyosarcoma; rhabdomyosarcoma; teratoma; hemangiosarcoma; Kaposi sarcoma; lymphangiosarcoma; bone osteoma; osteosarcoma; osteogenic sarcoma; chondrosarcoma; meningioma; non-Hodgkin lymphoma; Hodgkin lymphoma; and leukemia.

As used herein, the term "nucleotide" is used as a noun to refer to individual nucleotides or varieties of nucleotides as opposed to a nucleotide sequence. Illustrative examples of nucleic acid-based agents include antisense molecules such as antisense oligonucleotides and polynucleotides; catalytic nucleic acid-based agents, such as ribozymes; and nucleic acid-based aptamers.

As used herein, the term "nucleic acid" refers to RNA or DNA molecules having more than one nucleotide in any form including single-stranded, double-stranded, oligonucleotide or polynucleotide. The term "nucleotide sequence" is used to refer to the ordering of nucleotides in an oligonucleotide or polynucleotide in a single-stranded form of nucleic acid.

The terms "duplex" and "double-stranded" are used to refer to nucleic acids characterized by binding interaction of complementary nucleotide sequences. A duplex includes a "sense" strand and an "antisense" strand. Such duplexes include RNA/RNA, DNA/DNA or RNA/DNA types of duplexes. A duplex may be formed from two nucleotide sequences which are otherwise unconnected. Alternatively, a duplex may be formed by a single-stranded nucleic acid where the single-stranded nucleic acid has substantially complementary sense and antisense regions. Such a nucleic acid forms a "hairpin" conformation when the substantially complementary sense and antisense regions are hybridized to form a duplex.

In certain embodiments of the invention, the BL promoter is operatively coupled to a suicide gene such as thymidine kinase. In this context, transfection of the herpes simplex virus type-1 thymidine kinase gene (HTK), given in combination with the drug ganciclovir (GCV), is the most commonly used cancer gene therapy system to date, both in experimental models and clinical trials. See J. Gomez-Navarro et al., "Gene therapy for cancer," European Journal of Cancer, vol. 35, pp. 867-885 (1999). HTK, whose substrate specificity is distinct from that of cellular thymidine kinases, can convert GCV to the toxic phosphorylated form, specifically killing the cells that express HTK. Since the concept of an HTK/GCV system was first described, it has shown good success as a tumor ablation strategy in a variety of experimental models. In addition, over two dozen clinical gene therapy trials based on this model have been initiated in the last seven years. See J. A. Roth et al., "Gene therapy for cancer: what have we done and where are we going?" Journal of the National Cancer Institute, vol. 89(1), pp. 21-39 (1997); D. Klatzmann et al., "A Phase I/II dose-escalation study of herpes simplex virus type 1 thymidine kinase "suicide" gene therapy for recurrent metastatic melanoma," Human Gene Therapy, vol. 9, pp. 2585-2894 (1998); and J. R. Herman et al., "In situ gene therapy for adenocarcinoma of the prostate: A phase I clinical trial," Human Gene Therapy, vol. 10, pp. 1239-1249 (1999).

As used herein, the term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand. The degree of complementarity, also called homology, between nucleic acid strands significantly affects binding of the strands to each other. An antisense strand which is substantially complementary to a sense strand hybridizes to the sense strand under high stringency hybridization conditions.

As used herein, the term "hybridization" refers to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols, 5th Ed., 2002. High stringency hybridization conditions are those that only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

As used herein, the term "specific hybridization" refers to hybridization of a particular nucleic acid to a target nucleic acid without substantial hybridization to nucleic acids other than the target nucleic acid in a cell, tissue or subject.

As used herein, the terms "expression construct" and "expression cassette" as used refer to a double-stranded recombinant DNA molecule containing a desired nucleic acid coding sequence encoding an DNA, RNA, siRNA or shRNA and containing appropriate regulatory elements necessary or desirable for the transcription of the operably linked coding sequence in vitro or in vivo.

The term "regulatory element" as used herein refers to a nucleotide sequence which controls some aspect of the expression of nucleic acid sequences. Exemplary regulatory elements illustratively include an enhancer, an internal ribosome entry site, an origin of replication, a polyadenylation signal, a promoter, a transcription termination sequence, and an upstream regulatory domain, which contribute to the replication, transcription, post-transcriptional processing of a nucleic acid sequence.

As used herein, the term "operably linked" refers to connection of two or more nucleic acid molecules, including an oligonucleotide or polynucleotide to be transcribed and a regulatory element such as a promoter or an enhancer element, which allows transcription of the oligonucleotide or polynucleotide to be transcribed.

As used herein, the term "promoter" refers to a DNA sequence that can be operably linked to another nucleic acid sequence so that this other sequence is transcribed. A promoter is generally positioned upstream of a nucleic acid sequence to be transcribed and provides a site for specific binding by RNA polymerase and other transcription factors. In specific embodiments, a promoter is generally positioned upstream of the nucleic acid sequence transcribed to produce DNA, RNA, siRNA or shRNA, and provides a site for specific binding by RNA polymerase and other transcription factors. For example, regulatory elements include C2, E2, G2, A3, CRE1, GG2, A2, C1, E1, A1 domains. And various repeats and arrangements thereof, for example, C2/E2/G2/A3/CRE1 and GG2/A2/C1/E1/A1 or one, two or three repeated of C2/E2/G2/A3/CRE1 and one, two or three repeated of GG2/A2/C1/E1/A1.

As used herein, the term "recombinant" denotes a nucleic acid construct in which two or more nucleic acids are linked and which are not found linked in nature. The present invention also relates to a method of gene targeting or homologous recombination in cells and the resulting primary, secondary, or immortalized cells. The present invention is particularly useful for turning on the expression of genes, which comprise native transcription units which are sufficiently large that they are difficult to isolate and express, or for turning on genes for which the entire protein coding region is unavailable or has not been cloned. The present invention also describes a method by which homologous recombination is used to convert a gene into a cDNA copy, devoid of introns, for transfer into yeast or bacteria for in vitro protein production.

The present invention and the methods described in the applications incorporated herein by reference relate to cells transfected with exogenous genetic material (DNA or RNA) which encodes a clinically useful product that includes proteins, enzymes, hormones, cytokines, antigens, antibodies, enzymes, clotting factors, transport proteins, receptors, regulatory proteins, structural proteins, transcription factors, or anti-sense RNA. Additionally, the methods of the present invention can be used to produce cells, which produce non-naturally occurring ribozymes, proteins, or nucleic acids. The present invention also relates to a method of activating a gene, which is present in cells, but is not normally expressed in the cells or is not expressed at significant levels in the cells. The present invention can be used in homologous recombination or targeting to replace or disable the regulatory region normally associated with the gene with a regulatory sequence which causes the gene to be expressed at levels higher than evident in the corresponding nontransfected cell, or causes the gene to display a pattern of regulation or induction that is different than evident in the corresponding nontransfected cell.

Exogenous DNA incorporated into cells by the present method is: DNA which encodes a translation or transcription product whose expression in cells is desired, or a portion of a translation or transcription product, such as a protein product or RNA product useful to treat an existing condition or prevent it from occurring; or DNA which does not encode a gene product but is itself useful, such as a transcriptional regulatory sequence or DNA useful to treat an existing condition or prevent it from occurring. Exogenous DNA can be, for example, a hormone, a cytokine, an antigen, an antibody, an enzyme, a clotting factor, a transport protein, a receptor, a regulatory protein, a structural protein, a transcription factor, an anti-sense RNA, or a ribozyme. Additionally, the product can be a protein or a nucleic acid which does not occur in nature (i.e., a novel protein or novel nucleic acid). The DNA can be obtained from a source in which it occurs in nature or can be produced, using genetic engineering techniques or synthetic processes. The DNA can encode one or more therapeutic products.

DNA constructs (alternatively, nucleic acid constructs), which include exogenous DNA and, optionally, DNA encoding a selectable marker, along with additional sequences necessary for expression of the exogenous DNA in recipient cells, are used to transfect cells in which the encoded product is to be produced. The DNA construct can also include targeting sequences for homologous recombination with host cell DNA. DNA constructs which include exogenous DNA sequences, which do not encode a gene product and, optionally, include DNA encoding a selectable marker. The DNA constructs may be introduced into cells by a variety of methods, including electroporation, microinjection, calcium phosphate precipitation, and liposome-polybrene- or DEAE dextran-mediated transfection, infectious vectors, e.g., retroviral, herpes, adenovirus, adenovirus-associated, mumps and poliovirus vectors, can be used to introduce the DNA. The cells produced by the present invention are useful for in vitro production of therapeutic products, which can be purified and delivered by conventional pharmaceutics routes.

The present invention of providing a delivery system for treating an individual with an abnormal or undesirable condition which responds to delivery of a therapeutic product, which is either: a therapeutic protein (e.g., a protein which is absent, underproduced relative to the individual's physiologic needs, and/or a protein that is defective or inefficiently or inappropriately utilized in the individual, and/or a protein with novel functions, such as enzymatic or transport functions) or a therapeutic nucleic acid (e.g., DNA which binds to or sequesters a regulatory protein, RNA which inhibits gene expression or has intrinsic enzymatic activity).

A nucleic acid construct is directed to a specified target sequence of a nucleic acid molecule encoding a nucleic acid sequence. The nucleic acid sequence may also be directed to a nucleic acid sequence encoding a variant of the protein shown. Variants include naturally occurring allelic variants or non-naturally occurring allelic variants. Such naturally occurring and non-naturally occurring variants include proteins having amino acid deletions, substitutions and additions, as well as fragments, derivatives or analogs.

The present invention includes a nucleic acid construct having a regulatory element or promoter region operably linked to an exogenous DNA or RNA segment. Alternatively, the nucleic acid construct may have a regulatory element operably linked to an exogenous DNA insertion point.

The nucleic acid construct of the present invention may be of any construct known to the skilled artisan that can be introduced into a cell by any of various methods known in the art. For example, a nucleic acid is introduced into a cell via calcium phosphate or calcium chloride co-precipitationmediated transfection, DEAE-dextran-mediated transfection, liposome-mediated transfection, electroporation and microinjection.

The present invention provides a DNA promoter sequence operably linked to a nucleic acid sequence to be transcribed such as a nucleic acid sequence, for example, regulatory elements include C2, E2, G2, A3, CRE1, CRE2, GG2, GG1, A2, C1, E1, A1, G1 domains and various repeats and arrangements thereof.

The present invention provides a nucleic acid construct having promoter activity that includes a BL promoter comprising at least one E2/A3 motif and an exogenous nucleic acid fragment operably linked to the BL promoter, wherein the BL promoter regulates the expression of an exogenous nucleic acid fragment.

The BL promoter may include at least one A2/E1/A1 motif; at least one C2/E2/G2/A3/CRE1 motif and at least one GG2/A2/C1/E1/A1 motif; at least one, two or three repeated of C2/E2/G2/A3/CRE1 motifs and at least three repeated GG2/A2/C1/E1/A1 motifs; at least one five repeated C2/E2/G2/A3/CRE1 motifs or a combination thereof. The BL promoter may be a BL-1 promoter, a BL-4 promoter or other BL promoter; however the BL promoter may be a HIP promoter. The exogenous nucleic acid fragment encodes for proteins, enzymes, hormones, cytokines, antigens, antibodies, enzymes, clotting factors, transport proteins, receptors, regulatory proteins, structural proteins, transcription factors, anti-sense RNA. In one embodiment the exogenous nucleic acid fragment encodes a toxin (e.g., herpes thymidine kinase) translated to kill a cell (e.g., cancer cell). The cancer cell may be a metastatic tumor selected from the group consisting of bladder, breast, cervical, colon, lung, prostate, and head and neck. In general, the exogenous nucleic acid fragment is delivered to a host cell and under conditions that overexpress the exogenous nucleic acid fragment at a level greater relative to a normal cell level.

The present invention also provides an expression vector for expression of an exogenous nucleic acid having a BL promoter comprising at least one E2/A3 motif; and an exogenous nucleic acid fragment insertion site operably linked to the BL promoter, wherein the BL promoter regulates the expression of an exogenous nucleic acid fragment inserted at the exogenous nucleic acid fragment insertion site.

The present invention also provides a transgenic cell comprising the nucleic acid construct having promoter activity that includes a minimal promoter comprising at least one E2/A3 motif and an exogenous nucleic acid fragment operably linked to the minimal promoter, wherein the minimal promoter regulates the expression of an exogenous nucleic acid fragment.

A nucleic acid construct of the present invention includes −360 bp to +1 of the Human Insulin Promoter (HIP) promoter (and a truncates and mutations thereof) operably linked to an exogenous nucleic acid fragment. The HIP includes an A box and E box that are significant elements for the activation of wild type insulin promoters. It is the interactions among elements that give the full function of the promoter. The construct may also include repeated A/E mini enhancer that induces enhanced promoter activity.

FIG. 1A is an image of the promoter sequence elements in the insulin promoter. FIG. 1B an image of the sequence of the BL 1 promoter sequence and FIG. 1C a sequence of the BL 1 promoter sequence showing the promoter elements and the relative locations thereof. FIG. 1D a sequence of the BL 4 promoter sequence. The nucleic acid construct of the present invention also includes a BL promoter operably linked to an exogenous nucleic acid fragment. The BL promoter includes a 600 bp sequence with a core E2/A3 motif.

The nucleic acid construct of the present invention also includes a BL 1 promoter operably linked to an exogenous nucleic acid fragment. The BL 1 promoter includes a 550 bp sequence which is composed of three repeated of C2/E2/G2/A3/CRE1 motifs and three repeated GG2/A2/C1/E1/A1 motifs. The BL promoter includes a core sequence of E2/A3 and A2/E1/A1 motifs.

The nucleic acid construct of the present invention also includes a BL 4 promoter operably linked to an exogenous nucleic acid fragment. The BL 4 promoter includes a 423 bp sequence with five repeated C2/E2/G2/A3/CRE1 motifs with a core sequence motif of E2/A3.

In one embodiment, a method according to the present invention includes a tumor cell with an effective amount of an agent introduced into the tumor cell by the exogenous nucleic acid fragment of the nucleic acid construct controlled by the BL 1 promoter.

FIG. 2 is a plot of the CAT assay for HIP activity in Beta TC-6 cells. These data compare the human insulin promoter fragments to the 508 bp rat insulin promoter fragment to drive expression of CAT reporter in mouse insulinoma cells. The human insulin promoter fragments drive far greater expression of CAT than the RIP.

Figure 3:
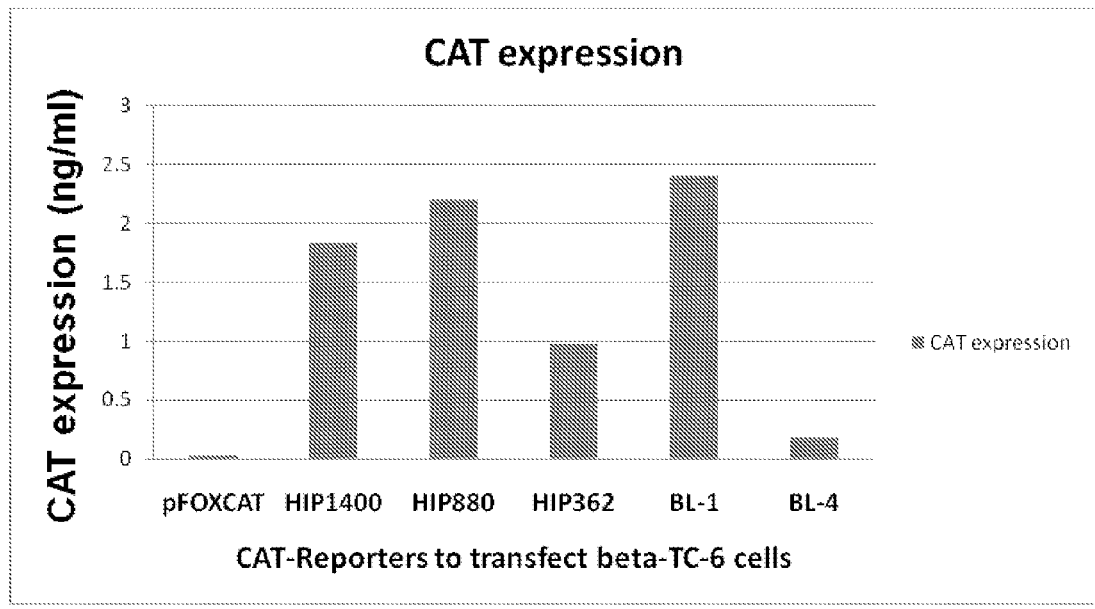
FIG. 3 is a plot of the CAT assay for BL promoter expression activity in Beta TC-6 cells.

FIG. 3 is a plot of the CAT assay for HIP promoter construct expression activity BL promoter construct expression activity in Beta TC-6 cells. These data demonstrate that the synthetic BL-1 promoter, but not the BL-4 promoter, induces expression of CAT equal to or better than human insulin promoter fragments in this mouse insulinoma cell line.

Figure 4:
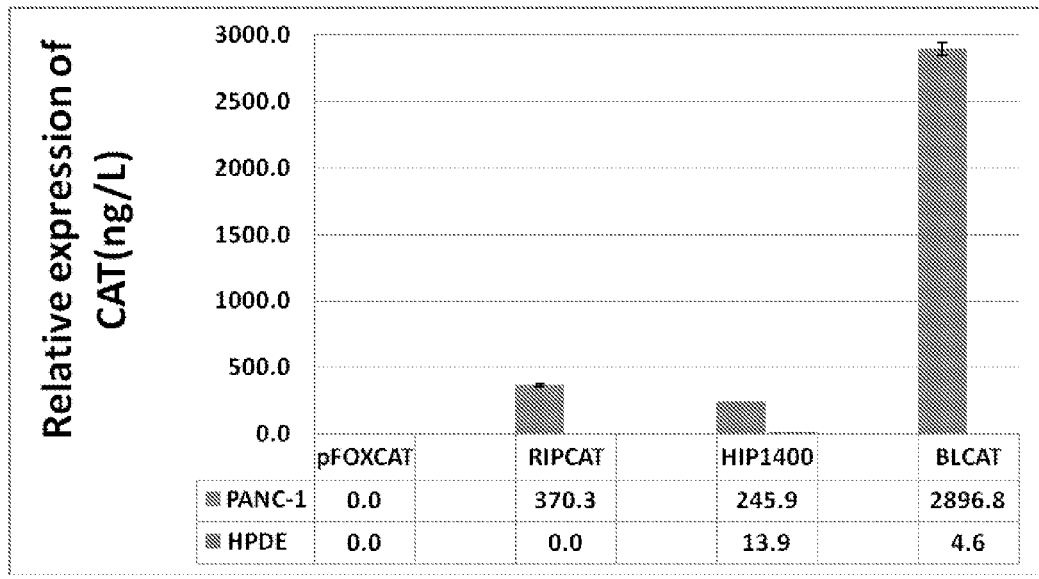
FIG. 4 is a plot of the assay of the relative CAT expression for HIP and BL activity in PANC-1 and HPDE cells.

FIG. 4 is a plot of the assay of the relative CAT expression being driven by BL-1 promoter compared to RIP and HIP 1400 promoter constructs in human pancreas cancer cell line, PANC-1, which have high expression of PDX-1, and benign human pancreatic ductal epithelial cell line HPDE, which have no expression of PDX-1 and are a negative control cell line. The data demonstrate that BL-1 drives expression of CAT in human pancreas cancer cell lines that overexpress PDX-1 to a far greater degree than HIP and RIP, suggesting that BL could be used to drive gene expression in pancreas cancer cells that overexpress PDX-1, which is the key transcription factor activating BL.

Figure 5:
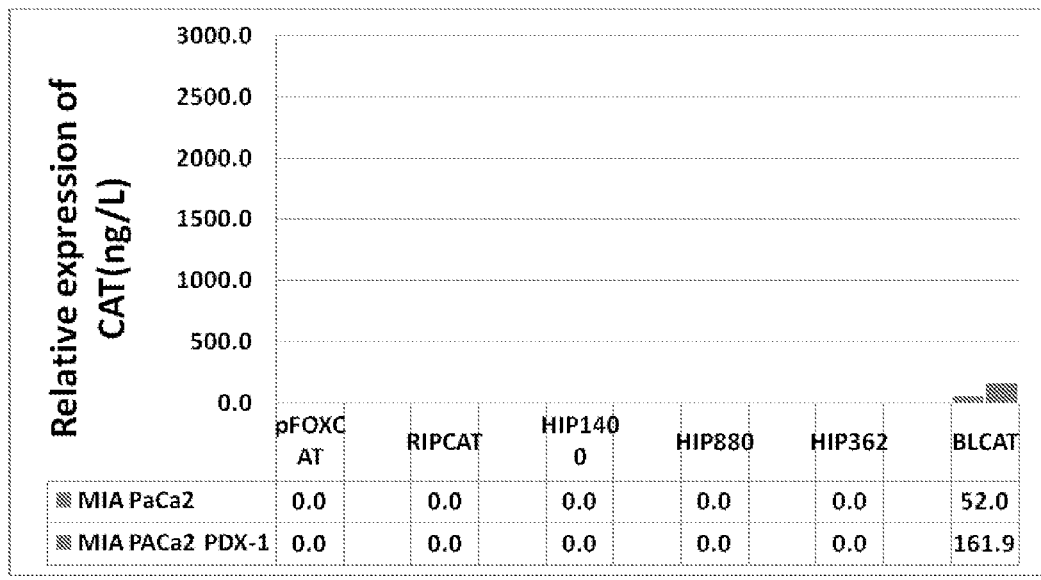
FIG. 5 is a plot of the assay of the relative CAT expression for MIA PaCa2 vs MIA PaCa2 PDX-1 activity in Mia PaCa2 cells.

FIG. 5 is a plot of the assay of the relative CAT expression being driven by BL-1 promoter compared to RIP and three HIP fragments in human pancreas cancer cell line, MIA PaCa2, which have very low PDX-1 expression vs MIA PaCa2 cells stably transfected with PDX-1. These data demonstrate the BL-1 is more effective than RIP or HIP in driving gene expression in human pancreas cancer cells with low PDX-1 expression.

Figure 6:
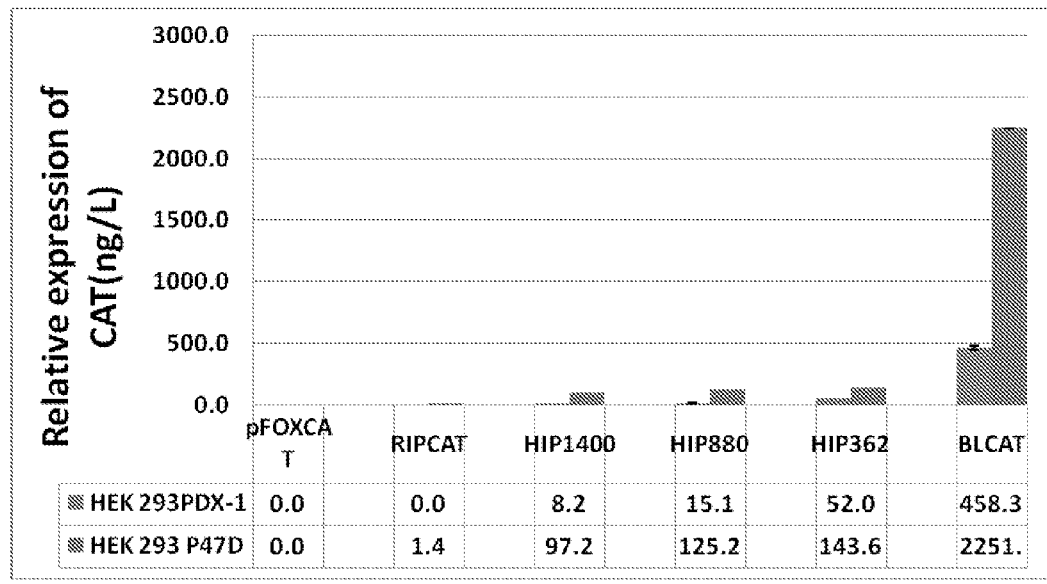
FIG. 6 is a plot of the assay of the relative CAT expression for 293 PDX-1 vs 293 P47D activity in HEK-293 cells.

FIG. 6 is a plot of the assay of the relative CAT expression being driven by BL-1 promoter compared to RIP and three HIP fragments in human embryonic kidney cell line 293, (which have no PDX-1 expression), stably transfected with PDX-1 or mutated PDX-1 P47D. These data demonstrate the BL-1 is far more effective than RIP or HIP in driving gene expression in human embryonic kidney cells that have overexpression of PDX-1 or mutated PDX-1 P47D.

Figure 7:
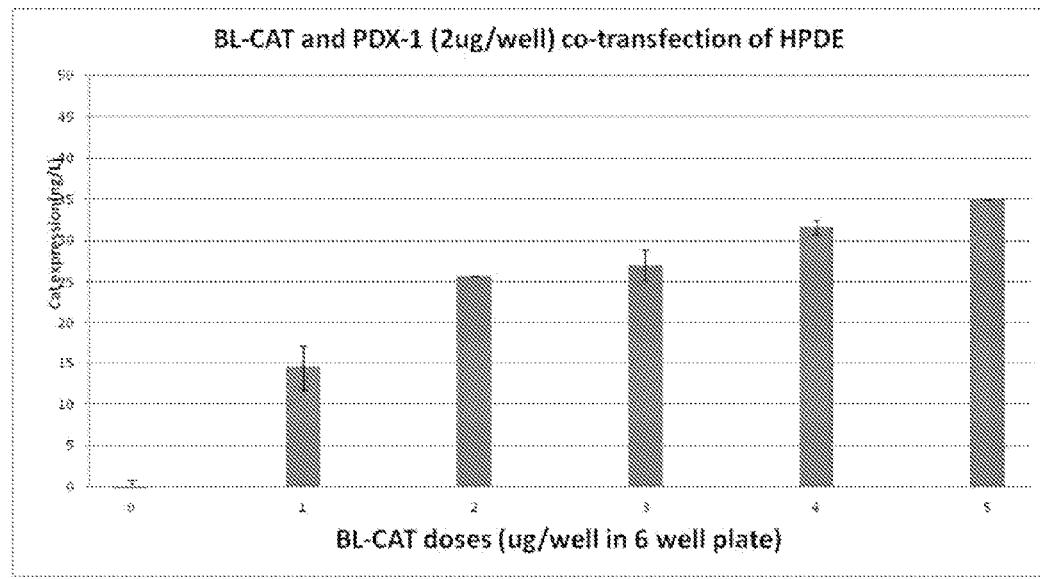
FIG. 7 is a plot of the assay of the BL-CAT dose curve in expression verses dose in HPDE cells.

FIG. 7 is a plot of the assay of the BL-CAT driving CAT expression in response to increasing doses of PDX-1 in human pancreatic ductal epithelial cells, which have very low expression of PDX-1. The data demonstrate that BL requires PDX-1 to drive expression of CAT in human pancreatic ductal epithelial cells.

Figure 8:
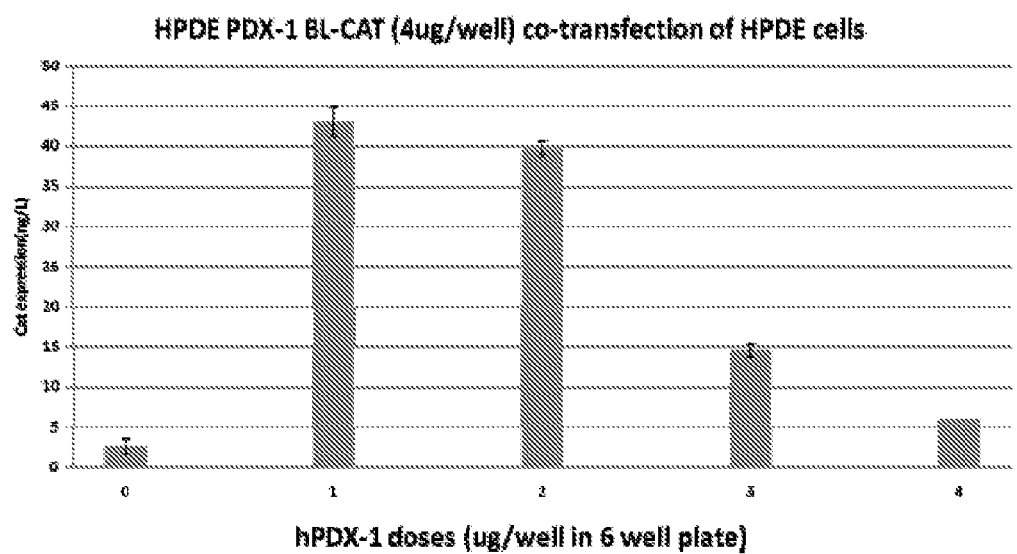
FIG. 8 is a plot of the assay of the PDX-1 dose curve in expression verses dose in HPDE cells.

FIG. 8 is a plot of another assay of the BL-CAT driving CAT expression in response to increasing doses of PDX-1 in human pancreatic ductal epithelial cells, which have very low expression of PDX-1. The data also demonstrate that BL requires PDX-1 to drive expression of CAT in human pancreatic ductal epithelial cells.

Figure 9:
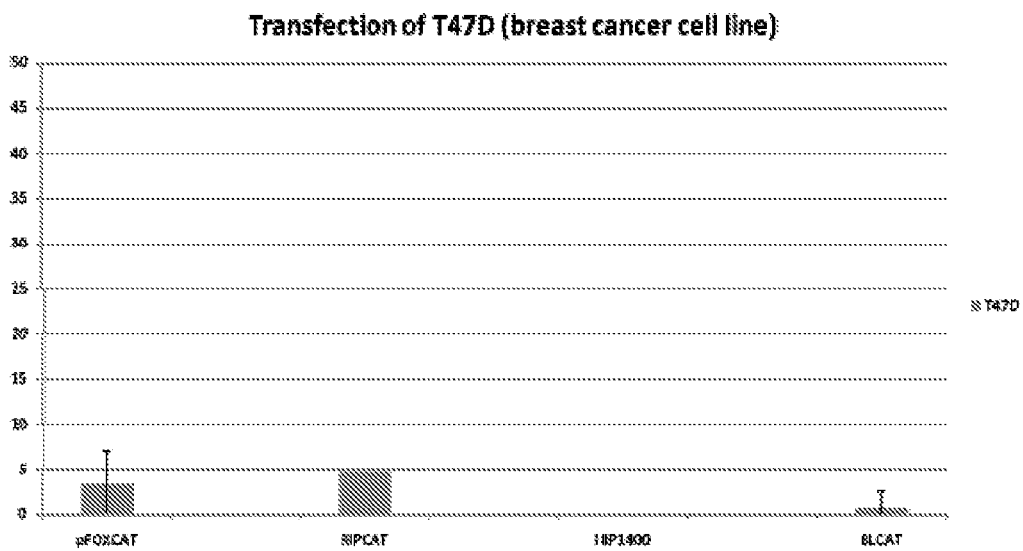
FIG. 9 is a plot of the assay of the BL-CAT transfection of T47D cells.

FIG. 9 is a plot of the assay of the BL driving expression of CAT compared to RIP and HIP in the human breast cancer cell line, T47D, which have low expression levels of PDX-1. These data demonstrate that BL is capable of driving CAT expression in human breast cancer cell lines that have low PDX-1 expression, although the level of CAT expression is low.

Figure 10:
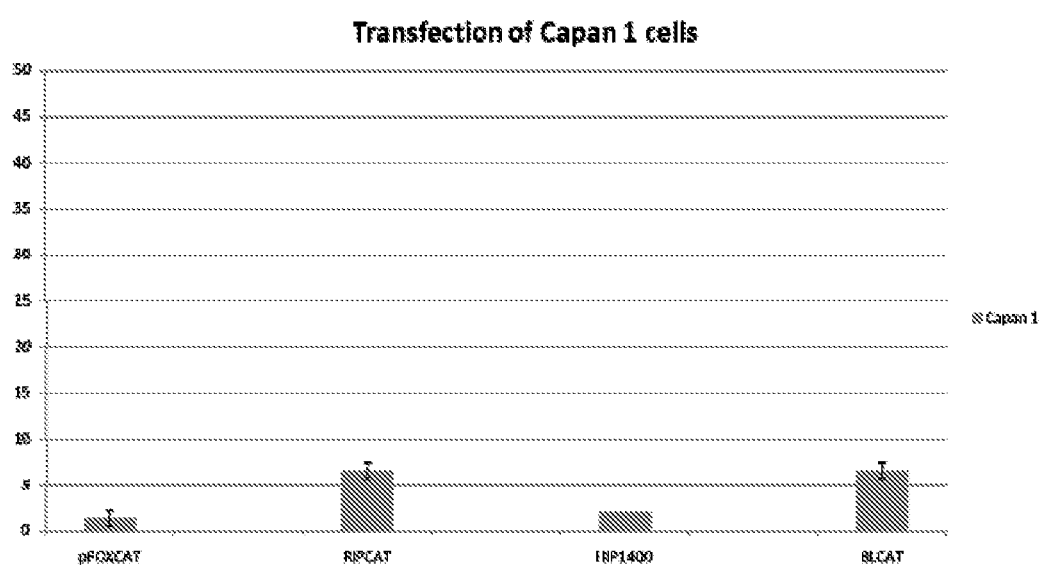
FIG. 10 is a plot of the assay of the BL-CAT transfection of CAPAN-1 cells.

FIG. 10 is a plot of the assay of the BL-CAT driving expression of CAT compared to RIP and HIP in the human pancreas cancer cell line, CAPAN-1, which have moderate expression levels of PDX-1. These data demonstrate that BL is capable of driving CAT expression in another human pancreas cancer cell lines that have moderate PDX-1 expression.

Figure 11:
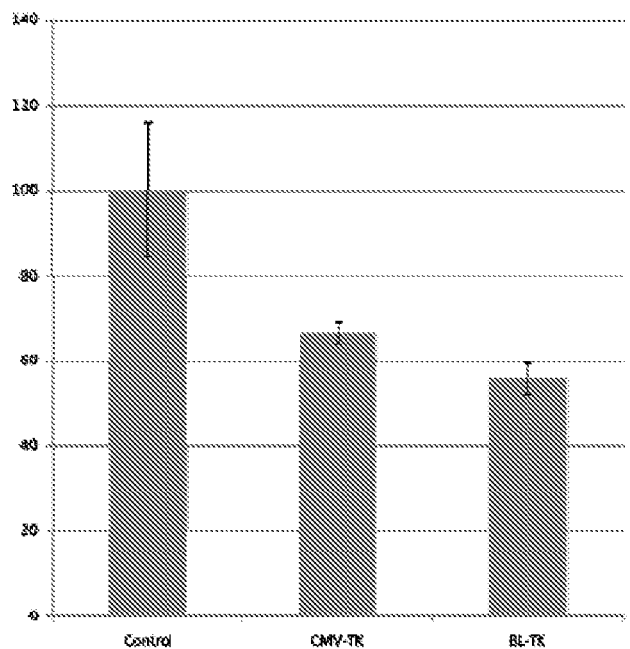
FIG. 11 is a plot comparing promoter activities and cytotoxic effect of BL-TK and GCV versus CMV-TK and GCV in PANC-1 cells.

FIG. 11 is a plot illustrating the cytotoxicity of BL-TK and ganciclovir (GCV) versus CMV-TK and GCV on the human pancreas cancer cell line, PANC-1, which have high PDX-1 expression. Cytotoxic effect on PANC-1 cells is by MTS assay. PANC-1 cells were treated with ganciclovir (25 ug/ml) after 24 hours of transfection with BL-TK, CMV-TK or empty vector, respectively. 72 hours after transfection, MTS assay was performed to test the cell viability. These data demonstrate the BL promoter is equal to the CMV promoter in driving TK expression in these human pancreas cancer cell lines and in causing a cytotoxic effect on these cells after treatment with GCV. The data support the concept of replacing the cytomegalovirus promoter with the human BL promoter in a variety of contexts, for example, in applications involving gene and RNAi delivery and expression.

Figure 12:
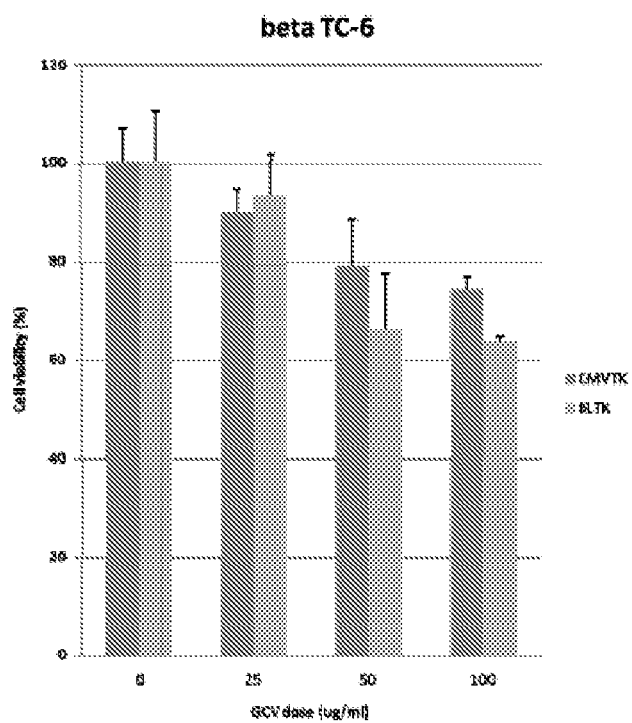
FIG. 12 is a plot comparing promoter activities and cytotoxic of BL-TK and GCV versus CMV-TK and GCV in Beta TC-6 cells.

FIG. 12 is a plot illustrating the cytotoxicity of BL-TK and ganciclovir (GCV) versus CMV-TK and GCV on the mouse insulinoma cell line, Beta TC-6, which have high PDX-1 expression. Cytotoxic effect on Beta TC-6 cells is by MTS assay. Beta TC-6 cells were treated with ganciclovir (25 ug/ml) after 24 hours of transfection with BL-TK, CMV-TK or empty vector, respectively. 72 hours after transfection, MTS assay was performed to test the cell viability. These data demonstrate the BL promoter is equal to the promoter CMV in driving TK expression in these mouse insulinoma cell lines and in causing a cytotoxic effect on these cells after treatment with GCV. The data support the concept of replacing the cytomegalovirus promoter with the human BL promoter in a variety of contexts, for example, in applications involving gene and RNAi delivery and expression.

Figure 13:
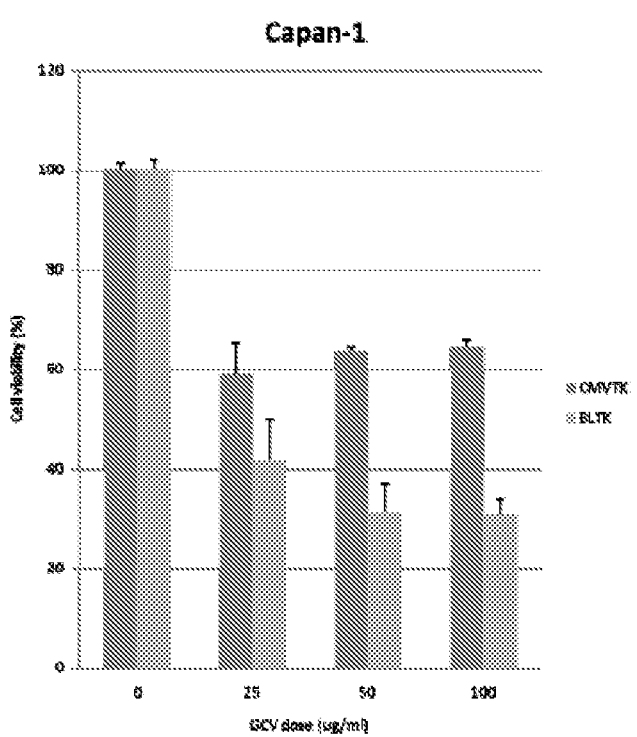
FIG. 13 is a plot comparing promoter activities and cytotoxic effect of BL-TK and GCV versus CMV-TK and GCV in CAPAN-1 cells.

FIG. 13 is a plot illustrating the cytotoxicity of BL-TK and ganciclovir (GCV) versus CMV-TK and GCV on the human pancreas cancer cell line, CAPAN-1, which have moderate PDX-1 expression. Cytotoxic effect on CAPAN-1 cells is by MTS assay. CAPAN-1 cells were treated with ganciclovir (25 ug/ml) after 24 hours of transfection with BL-TK, CMV-TK or empty vector, respectively. 72 hours after transfection, MTS assay was performed to test the cell viability. These data demonstrate the BL promoter is equal to the CMV promoter in driving TK expression in these human pancreas cancer cell lines and in causing a greater cytotoxic effect on these cells after treatment with GCV. These data support the concept of replacing the cytomegalovirus promoter with the human BL promoter in a variety of contexts, for example, in applications involving gene and RNAi delivery and expression.

FIG. 14 plot illustrating cell proliferation on human embryonic kidney cells stably overexpressing PDX-1 transfected with BL-Somatostatin Receptor 5 (BL-SSTR5) or CMV-SSTR5, then and treated with a SSTR5-specific agonist at 1 ng/ml. Cellular proliferation effect on HEK-293 cells was performed by MTS assay. HEK-293/PDX-1 cells were treated with somatostatin receptor 5 analogue (1 ng/ml) after 24 hours of transfection with BL-SSTR5, CMV-SSTR5 or empty vector, respectively. 72 hours after transfection, MTS assay was performed to test the cell proliferation. These data demonstrate the BL promoter is equal to the CMV promoter in driving SSTR5 expression in these human cell lines and in causing a greater antiproliferative effect on these cells after treatment with the SSTR5-specific agonist. These data support the concept of replacing the cytomegalovirus promoter with the human BL promoter in a variety of contexts, for example, in applications involving gene and RNAi delivery and expression.

FIG. 15 plot illustrating proliferation on mouse insulinoma Beta TC-6 cells, which have high PDX-1 overexpression, transfected with BL-SSTR5 or empty vector and treated with doses of SSTR5-specific agonist. Cellular proliferation effect on HEK-293 cells was performed by MTS assay. Beta TC-6 cells were treated with escalating doses of somatostatin receptor 5 analogue after 24 hours of transfection with BL-SSTR5 or empty vector, respectively. 72 hours after transfection, MTS assay was performed to test the cell proliferation. These data demonstrate the BL promoter drives functional SSTR5 expression in these mouse insulinoma cell lines and in causing a greater antiproliferative effect on these cells after treatment with the SSTR5-specific agonist. These data support the concept of using the BL promoter to drive expression of functional SSTR5 in a variety of contexts.

Figure 16:
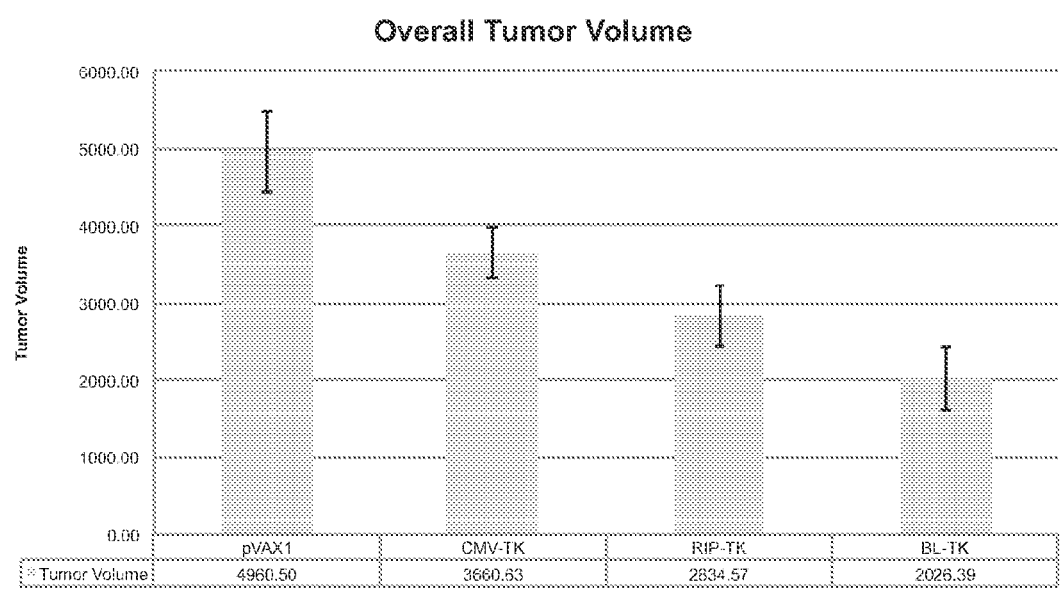
FIG. 16 is a plot illustrating the in vivo tumor targeting effect of BL-TK and GCV gene therapy in a xenograft mouse model of metastatic human pancreas cancer.

FIG. 16 plot illustrating the in vivo tumor targeting effect of BL-TK and GCV gene therapy in a xenograft mouse model of metastatic human pancreas cancer. At age of 2-3 months, 1 million human pancreas cancer cells, PANC-1 cells, which have high expression of PDX-1, were injected intraperitoneally into 65 immune deficient (SCID) mice; 1 month after PANC-1 cell injection, treatment was performed with a single intravenous injection of 35 ug liposomal plasmid BL-TK DNA, CMV-TK, RIP-TK or empty vector per mouse. The mice were then treated with the prodrug, GCV (50 ug/ml per mouse per day) for 14 days. After a 60 day period of observation, mice were sacrificed and intraperitoneal tumor volume was measured. The mice receiving BL-TK had the lowest PANC-1 tumor volume compared to RIP-TK, CMV-TK and empty vector controls after GCV treatment. These data demonstrate the in vivo effectiveness of systemic BL-TK gene therapy to markedly reduce tumor volume in a mouse model of metastatic pancreas cancer. These data support the concept of replacing the cytomegalovirus promoter with the human BL promoter in a variety of contexts, for example, in applications involving gene and RNAi delivery and expression.

The exogenous nucleic acid fragment can be any exogenous nucleic acid fragment. For example, the exogenous nucleic acid fragment may code for an anti-PDX-1 agent that includes peptide and protein anti-PDX-1 agents such as antibodies and peptide aptamers, as well as inhibitory compounds which are not peptides or proteins. An antibody or antibody fragment which is an anti-PDX-1 agent included in a composition and/or method of the present invention specifically binds to PDX-1 and inhibits activity of PDX-1.

Exogenous nucleic acid fragment may include fragments for RNA interference for inhibiting a selected gene. RNA interference has been characterized in numerous organisms and is known to be mediated by a double-stranded RNA, also termed herein a double-stranded RNA compound. Briefly described, RNA interference involves a mechanism triggered by the presence of small interfering RNA, siRNA, resulting in degradation of a target complementary mRNA. siRNA is a double-stranded RNA which includes a nucleic acid sequence complementary to a target sequence in the gene to be silenced. The double-stranded RNA may be provided as a long double-stranded RNA compound, in which case it is subject to cleavage by the endogenous endonuclease Dicer in a cell. Cleavage by Dicer results in siRNA duplexes having about 21-23 complementary nucleotides in each of the sense strand and the antisense strand, and optionally 1-2 nucleotides 3' overhangs on each of the two strands. As noted above, further details of siRNA compounds are described in Engelke, D. R., RNA Interference (RNAi): Nuts and Bolts of RNAi Technology, DNA Press LLC, Eagleville, Pa., 2003. Additional description of siRNA length and composition is found in Elbashir, S. M. et al., Genes and Devel., 15:188-200, 2001; and O'Toole, A. S. et al., RNA, 11:512-516, 2005.

The present invention provides a pharmaceutical composition that includes a nucleic acid construct according to the present invention and a pharmaceutically acceptable carrier. The term "pharmaceutically acceptable" refers to a material which can be administered to a subject along with a nucleic acid construct composition without causing significant undesirable biological effects and without interacting in a deleterious manner with any other component of the pharmaceutical composition.

Pharmaceutical compositions suitable for administration illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, and suitable mixtures thereof; vegetable oils such as olive oil; and injectable organic esters such as ethyloleate. Proper fluidity of liquids can be maintained, for example, by the use of a coating such as lecithin, by the maintenance of the required particle size in the case of dispersions, and by the use of surfactants.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity of injectables can be maintained, for example, by the use of a coating such as lecithin, by the maintenance of the required particle size in the case of dispersions and by the use of surfactants.

Pharmaceutical compositions according to the present invention may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Further exemplary adjuvants include immunostimulating adjuvants such as Freund's complete adjuvant; Freund's incomplete adjuvant; aluminum hydroxide such as commercially available as Alhydrogel, Accurate Chemical & Scientific Co., Westbury, N.Y.; and Gerbu adjuvant, available from C-C Biotech, Poway, Calif.

Solid dosage forms for oral administration include capsules, tablets, pills, powders, and granules. In such solid dosage forms, a nucleic acid construct is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol, and glycerol monostearate; h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Microencapsulated formulations of a nucleic acid construct are also contemplated.

Liquid dosage forms for oral administration include pharmaceutically acceptable emulsions, solutions, suspensions, syrups, and elixirs. In addition to a nucleic acid construct according to the present invention, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, a pharmaceutical composition according to the present invention can also include adjuvants, such as wetting agents, emulsifying and suspending agents, sweetening, flavoring, and perfuming agents.

Suspensions, in addition to a nucleic acid construct, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Further, specific details of pharmaceutical formulation can be found in Pharmaceutical Dosage Forms Tablets, eds. H. A. Lieberman et al. (New York: Marcel Dekker, Inc., 1989), Remington: The Science and Practice of Pharmacy, Lippincott Williams & Wilkins, 21st Ed., 2006; and in L. V. Allen, Jr. et al., Ansel's Pharmaceutical Dosage Forms and Drug Delivery Systems, 8th Ed. (Philadelphia, Pa.: Lippincott, Williams & Wilkins, 2004).

A composition including a nucleic acid construct is optionally delivered in conjunction with a second therapeutic and/or diagnostic agent in one embodiment. An effective amount of a therapeutic and/or diagnostic agent is administered to achieve a therapeutic and/or diagnostic goal, illustratively including amelioration of pain, inflammation, or other signs or symptoms of a particular condition of the subject. A therapeutic and/or diagnostic agent suitable in this regard illustratively includes an analgesic, an antibiotic, an antibody, an antigen, an anti-inflammatory, an anti-tumor agent, an antiviral, a gamma or beta radiation emitting species, an enzyme, and a hormone. The nucleic acid construct composition and second therapeutic and/or diagnostic agent may be administered together in one composition, or separately.

A conjugate of the present invention can be administered to a subject alone or as part of a pharmaceutical composition. Inventive conjugate compositions are suitable for administration to patients by a variety of systemic and local routes illustratively including intravenous, oral, parenteral, intramuscular, topical, subcutaneous and mucosal.

The dosage of an inventive pharmaceutical composition will vary based on factors such as the route of administration; the age, health, and weight of the subject to whom the composition is to be administered; the nature and extent of the subject's symptoms, if any; and the effect desired. Usually a daily dosage of an inventive conjugate is in the range of about 0.001 to 100 milligrams per kilogram of a subject's body weight. A daily dose may be administered as two or more divided doses to obtain the desired effect. An inventive pharmaceutical composition may also be formulated for sustained release to obtain desired results.

It is contemplated that any embodiment discussed in this specification can be implemented with respect to any method, kit, reagent, or composition of the invention, and vice versa. Furthermore, compositions of the invention can be used to achieve methods of the invention.

It will be understood to those of skill in the art that the unique characteristics of the BL associated sequences disclosed herein allow them to be adapted for a wide variety of uses. In illustrative embodiments of the invention, the BL associated sequences are used for theranostics for cancer, for diabetes and disorders of glucose regulation, for cell sorting, and for veterinary theranostics.

For example, imaging is an enormous field of healthcare for both human and animals. In this context, the BL associated sequences disclosed herein can be used in methods for imaging a number different cell types (e.g. PDX-1-expressing cells), for example by driving expression of imaging genes, such as vTK, the expression of which can be imaged using PET-CT scans, MRI genes, optical imaging genes, etc. In an illustration of this, the data in FIGS. 14 and 15 show BL driving expression of SSTR5, which confirms that BL associated sequences can be used to enhance imaging including radionuclide imaging with radioactive somatostatin analogues, such as octreotide scanning, for various cancers (e.g. PDX-1 expressing cancers). See, e.g. Ji et al., Med Sci Monit, 2011; 17 (8): RA169-176; and Bodei et al., J. Endocrinol. Invest. 32: 360-369, 2009, the contents of which are incorporated herein by reference. In certain embodiments of the invention, the BL associated sequences are used in pancreatic cancer and insulinoma tumor cells to drive optical imaging genes and/or vTK genes.

As noted above, certain embodiments of the invention are directed towards PDX-1 expressing cells. Many cancers over express PDX-1, as well as cells in the islet of Langerhans (see, e.g. Wang et al., World J. Surg. 29, 334-338 (2005), the contents of which are incorporated herein by reference). Because PDX-1 expressing cells include islets of Langerhans, BL associated sequences can be used for imaging and therapy of diseases of glucose regulation, such as hypoglycemia, diabetes and the like. In addition, PDX-1 is over expressed in almost all solid cancers (e.g. breast, neuroendocrine tumors, prostate, breast, pancreas, liver, colorectal, stomach, esophagus, intestinal cancer, kidney, lung cancers etc.). In addition, PDX-1 is overexpressed in stem cells, pleuripotent stem cells and mesenchyman stem cells. Consequently, embodiments of the invention are directed towards this subset of PDX-1 expressing cells, for example in methods that modulate the differentiation of these stem cells (see, e.g. Yuan et al. in Mol Biol Rep 37:4023, 2010, the contents of which are incorporated by reference).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification (e.g. German et al., Diabetes August 1995 vol. 44 no. 8 1002-1004; and Odagiri et al., J Biol Chem. 1996 Jan. 26; 271(4):1909-15) are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1

Illustrative Working Embodiments of the Invention

Our studies demonstrated rat insulin promoter fragment (RIP)-driven suicide gene therapy effectively ablated PC tumors in mice and PDX-1 overexpression in PC was responsible for activation of RIP. For translational purposes, a set of novel human synthetic promoters (BLs) based upon selected PDX-1 activation sites in the human insulin promoter (HIP) were designed, cloned, tested for activity and specificity in vitro, and tested for therapeutic potential in vivo in a metastatic PC mouse model.

In our methodological approach, activity and specificity of BLs were determined by CAT and mCherry assays in PDX-1+PC and HEK293 cell lines vs PDX-1—human pancreatic ductal epithelial (HPDE) cells. BL1 had the highest activity of expressing reporter genes, therefore, BL1-vTK in pVAX1 was transfected in PC cells, which were then treated with GCV. Cytotoxicity was determined by MTS assay. 1M PANC-1 cells were injected ip into 65 SCID mice; two weeks later, mice received BL1-vTK, RIP-vTK, CMV-vTK, or pVAX1 empty vector control (35 ug liposomal DNA/mouse/tail vein followed by two weeks of GCV (40 mg/kg, ip, bid; N=15/group). Glucose levels were measured on days 14 and 60 after treatment. Tumor volume was measured in each mouse. Statistical analysis was performed via paired T test; $p<0.05$=significant.

The results show that BL1-driven CAT and mCherry reporter expression in PDX-1 stably expressing PC and HEK cells were significantly greater than RIP-driven expression ($p<0.05$) and equal to CMV-driven expression. No CAT expression was detected in PDX-1-negative cell lines, however, co-transfection of PDX-1 into HPDE cells resulted in CAT expression in a dose dependent manner. BL1-vTK was expressed in PC cells via Western blot and BL1-vTK/GCV treatment resulted in significant cytotoxic effect on PANC-1 and Capan-1 cells compared to controls ($p<0.05$). In the PANC-1 SCID mice, BL1-vTK/GCV significantly suppressed mean tumor volume (2026±422.3 mm3; $p<0.05$) vs RIP-vTK/GCV (2835±393.2 mm3) vs CMV-vTK/GCV (3661±329.7 mm3) vs pVAX1/GCV control (4961±517.4 mm3), ($p<0.05$; figure). Glucose levels were 221±29.0, 176±43.3, 110±7.4 and 107±19.2 mg/dl on day 14 and 192±29.6, 135±33.1, 204±42.2 and 109±15.2 mg/dl on day 60 after BL1-vTK/GCV, RIP-vTK/GCV, CMV-vTK/GCV and pVAX1/GCV, respectively.

In conclusion, BL1 successfully drives gene expression in PDX-1+PC cells with similar expression efficiency as the CMV promoter. Systemic BL1-vTK/GCV suicide gene therapy successfully targeted and suppressed PC tumor volume in a metastatic SCID mouse model with predictable off target effect of diabetes. The data from this study provides further evidence that BL1 has translational potential for PC targeted gene therapy.

What is claimed is:

1. A nucleic acid comprising:
    a BL promoter having at least three copies of a nucleotide sequence comprising nucleotide sequence motifs GG2, A2, C1, E1, A1 linked in an order: GG2/A2/C1/E1/A1, wherein:
    GG2 comprises GGAAAT (SEQ ID NO: 9);
    A2 comprises GGAAAT (SEQ ID NO: 10);
    C1 comprises TGCAGCCTCAGCC (SEQ ID NO: 11);
    E1 comprises GCCATCTGCC (SEQ ID NO: 12);
    A1 comprises TAAT (SEQ ID NO: 13);
    the nucleotide sequence motifs are separated by 0 to 20 nucleotides;
    the BL promoter modulates transcription of an heterologous nucleic acid operatively linked to the BL promoter.

2. The nucleic acid of claim 1, wherein the BL promoter further includes at least one nucleotide sequence comprising C2, E2, G2, A3, CRE1, CRE2, CRE3, G1 or an enhancer core, wherein:
    C2 comprises CAGGGACAGG (SEQ ID NO: 6);
    E2 comprises GCCACCGG (SEQ ID NO: 7);
    G2 comprises GGGCCC (SEQ ID NO: 8);
    A3 comprises TAAT (SEQ ID NO: 13);
    CRE1 comprises GACCCGCTGGTCC (SEQ ID NO: 16);
    CRE2 comprises TGACGACCAAGGAGATC (SEQ ID NO: 17);
    CRE3 comprises TGCATCAGAAGAG (SEQ ID NO: 18);
    CRE4 comprises TGCGTCAGGTGGGCT (SEQ ID NO: 19);
    G1 comprises GTAGGGGA (SEQ ID NO: 15); and
    the enhancer core comprises TGGAAAG (SEQ ID NO: 5).

3. The nucleic acid of claim 2, wherein the BL promoter comprises:
    a BL-1 promoter as shown in SEQ ID NO: 1; or
    a BL-4 promoter as shown in SEQ ID NO: 3.

4. A nucleic acid comprising:
    a BL promoter having at least three copies of a nucleotide sequence comprising nucleotide sequence motifs GG2, A2, C1, E1, A1 linked in an order: GG2/A2/C1/E1/A1, wherein:
    GG2 comprises GGAAAT (SEQ ID NO: 9);
    A2 comprises GGAAAT (SEQ ID NO: 10);
    C1 comprises TGCAGCCTCAGCC (SEQ ID NO: 11);
    E1 comprises GCCATCTGCC (SEQ ID NO: 12);
    A1 comprises TART (SEQ ID NO: 13);
    the nucleotide sequence motifs are separated by 0 to 20 nucleotides;
    the BL promoter modulates transcription of an heterologous nucleic acid operatively linked to the BL promoter; and
    a heterologous nucleic acid operatively linked to the BL promoter, wherein the heterologous nucleic acid encodes a polypeptide sequence.

5. An expression vector comprising the nucleic acid of claim 1.

6. A host cell comprising the vector of claim 5.

7. The host cell of claim 6 wherein the cell is an *Escherichia coli*, yeast or human cancer cell.

8. A composition of matter comprising the nucleic acid of claim 1 and a pharmaceutically acceptable carrier.

9. A nucleic acid comprising a BL-1 promoter as shown in SEQ ID NO: 1.

10. The nucleic acid of claim 9, wherein the BL-1 promoter is operatively coupled to a heterologous nucleic acid sequence.

\* \* \* \* \*

SEQUENCE LISTING

```
<160> NUMBER OF SEQ ID NOS: 19

<210> SEQ ID NO 1
<211> LENGTH: 550
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gacagcagcg caaagagccc cgccctgcag cctccagctc tcctggtcta atgtggaaag      60
tggcccaggt gagggctttg ctctcctgga gacatttgcc cccagctgtg agcagggaca    120
ggtctggcca ccgggcccct ggttaagact ctaatgaccc gctggtccca gggacaggtc    180
tggccaccgg gccctggtt aagactctaa tgaccgctg gtcccaggga caggtctggc     240
caccgggccc ctggttaaga ctctaatgac ccgctggtcc ggaaatggtc cggaaattgc     300
agcctcagcc cccagccatc tgccgacccc ccacccccag gccctaatgg gcggaaatgg     360
tccggaaatt gcagcctcag cccccagcca tctgccgacc ccccaccccc aggccctaat     420
```

```
gggcggaaat ggtccggaaa ttgcagcctc agccccagc catctgccga ccccccacc      480 ccaggcccta atgggcggta ggggagatgg gctctgagac tataaagcca gcggggccc      540 agcagccctc                                                             550
```

```
<210> SEQ ID NO 2
<211> LENGTH: 700
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
```

```
acagggtgt ggggacaggg gtgtggggac aggggtctgg ggacaggggt gtgggacag        60 gggtcctggg gacaggggtg tgggatagg ggtgtgggga caggggtgtg ggacagggg      120 tgtggggaca ggggtctggg gacagcagcg caaagagccc cgccctgcag cctccagctc    180
tcctggtcta atgtggaaag tgcccaggt gagggctttg ctctcctgga gacatttgcc    240
cccagctgtg agcagggaca ggtctggcca ccgggcccct ggttaagact ctaatgaccc    300
gctggtcctg aggaagaggt gctgacgacc aaggagatct cccacagac ccagcaccag    360 ggaaatggtc cggaaattgc agcctcagcc cccagccatc tgccgacccc ccacccccag    420
gccctaatgg gccaggcggc aggggttgag aggtagggga gatgggctct gagactataa    480
agccagcggg ggcccagcag ccctcagccc tccaggacag gctgcatcag aagaggccat    540
caagcaggtc tgttccaagg gcctttgcgt caggtgggct caggattcca gggtggctgg    600
accccaggcc ccagctctgc agcagggagg acgtggctgg gctcgtgaag catgtggggg    660
tgagcccagg ggccccaagg cagggcacct ggccttcagc                            700
```

```
<210> SEQ ID NO 3
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
gacagcagcg caaagagccc cgccctgcag cctccagctc tcctggtcta atgtggaaag     60 tgcccaggt gagggctttg ctctcctgga gacatttgcc cccagctgtg agcagggaca    120
ggtctggcca ccgggcccct ggttaagact ctaatgaccc gctggtccca gggacaggtc    180
tggccaccgg gcccctggtt aagactctaa tgacccgctg gtcccaggga caggtctggc    240
caccgggccc ctggttaaga ctctaatgac ccgctggtcc agggacagg tctggccacc    300 gggcccctgg ttaagactct aatgacccgc tggtcccagg gacaggtctg gccaccgggc    360
ccctggttaa gactctaatg acccgctggt ccctataaag ccagcggggg cccagcagcc    420
ctc                                                                   423
```

```
<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 4 tataaa                                                              6

<210> SEQ ID NO 5
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 tggaaag                                                             7

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cagggacagg                                                         10

<210> SEQ ID NO 7
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 gccaccgg                                                            8

<210> SEQ ID NO 8
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 gggccc                                                              6

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 ggaaat                                                              6

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 10 ggaaat                                                                 6

<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgcagcctca gcc                                                        13

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gccatctgcc                                                            10

<210> SEQ ID NO 13
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 taat                                                                   4

<210> SEQ ID NO 14
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 ggcg                                                                   4

<210> SEQ ID NO 15
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 gtagggg                                                                7

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 16
gacccgctgg tcc                                                      13

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgacgaccaa ggagatc                                                  17

<210> SEQ ID NO 18
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgcatcagaa gag                                                      13

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgcgtcaggt gggct                                                    15
```